United States Patent
Ashton-Rickardt

(10) Patent No.: US 12,173,030 B2
(45) Date of Patent: Dec. 24, 2024

(54) CAR-TREG-BASED THERAPIES FOR TREATING NEURODEGENERATIVE DISEASES

(71) Applicant: AZTHERAPIES, INC., Boston, MA (US)

(72) Inventor: Philip G. Ashton-Rickardt, Chestnut Hill, MA (US)

(73) Assignee: AZTherapies, Inc., Boston, MA (US)

( * ) Notice: Subject to any disclaimer, the term of this patent is extended or adjusted under 35 U.S.C. 154(b) by 1047 days.

(21) Appl. No.: 17/041,835

(22) PCT Filed: Mar. 21, 2019

(86) PCT No.: PCT/US2019/023395
§ 371 (c)(1),
(2) Date: Sep. 25, 2020

(87) PCT Pub. No.: WO2019/190879
PCT Pub. Date: Oct. 3, 2019

(65) Prior Publication Data
US 2021/0023137 A1    Jan. 28, 2021

Related U.S. Application Data

(60) Provisional application No. 62/648,684, filed on Mar. 27, 2018.

(51) Int. Cl.
*A61P 25/28* (2006.01)
*A61K 39/00* (2006.01)
*C07K 16/28* (2006.01)

(52) U.S. Cl.
CPC ...... *C07K 16/2803* (2013.01); *A61K 39/4611* (2023.05); *A61K 39/4621* (2023.05); *A61K 39/4631* (2023.05); *A61K 39/46432* (2023.05); *A61P 25/28* (2018.01); *A61K 2239/38* (2023.05); *C07K 2317/622* (2013.01); *C07K 2319/33* (2013.01)

(58) Field of Classification Search
CPC ..... A61K 35/17; A61P 25/28; C07K 16/2803; C07K 2317/622; C07K 2319/33
See application file for complete search history.

(56) References Cited

U.S. PATENT DOCUMENTS

| | | | |
|---|---|---|---|
| 8,790,642 B2 * | 7/2014 | Chen | A61P 1/04 530/387.3 |
| 9,040,669 B2 * | 5/2015 | Cheung | A61K 39/464453 530/387.9 |
| 9,896,510 B2 * | 2/2018 | Zhou | A61P 29/00 |
| 2008/0027001 A1 † | 1/2008 | Wood | |
| 2014/0024809 A1 | 1/2014 | Cheung et al. | |
| 2016/0184367 A1 | 6/2016 | Sackstein | |
| 2017/0210808 A1 * | 7/2017 | Rosenthal | C07K 16/286 |
| 2018/0117171 A1 | 5/2018 | Mooney et al. | |
| 2021/0023137 A1 | 1/2021 | Ashton-Rickardt | |
| 2023/0210899 A1 | 7/2023 | Watkin et al. | |

FOREIGN PATENT DOCUMENTS

| | | | | |
|---|---|---|---|---|
| WO | WO-2007140971 A2 * | 12/2007 | ......... | G01N 33/6896 |
| WO | WO 2012/156522 A1 | 11/2012 | | |
| WO | WO-2017100428 A1 * | 6/2017 | ............. | A61K 35/17 |

OTHER PUBLICATIONS

European Patent Office, Third Party Observation, Filed by Anonymous, EP Application No. 19776538.1, May 11, 2021, five pages.
PCT International Search Report and Written Opinion, PCT Application No. PCT/US2019/023395, Aug. 19, 2019, 10 pages.
Adair, P. R. et al. "Human Tregs Made Antigen Specific by Gene Modification: The Power to Treat Autoimmunity and Antidrug Antibodies with Precision." Frontiers in Immunology, vol. 8, Sep. 21, 2017, pp. 1-10.
European Patent Office, Extended European Search Report, EP Application No. 19776538.1, Dec. 21, 2021, 11 pages.
Fransson, M. et al. "CAR/FoxP3-Engineered T Regulatory Cells Target the CNS and Suppress EAE Upon Intranasal Delivery." Journal of Neuroinflammation, vol. 9, May 30, 2012, pp. 1-12.
Juan, M. et al. "Future of Chimeric Antigen Receptors (CARS): Could it Drive Solutions Beyond Cancer? Examples in Autoimmune Diseases." MOJ Immunology, vol. 5, No. 3, Mar. 17, 2017, pp. 1-3.
Li, T. et al. "Cell-Penetrating Anti-GFAP VHH and Corresponding Fluorescent Fusion Protein VHH-GFP Spontaneously Cross the Blood-Brain Barrier and Specifically Recognize Astrocytes: Application to Brain Imaging." The FASEB Journal, vol. 26, Oct. 2012, pp. 3969-3979.
Mekala, D. J. et al. "Immunotherapy of Autoimmune Encephalomyelitis with Redirected CD4+CD25+ T Lymphocytes." Blood, vol. 105, No. 5, Mar. 1, 2005, pp. 2090-2092.
Arjomandnejad, M. et al. "CAR-T Regulatory (CAR-Treg) Cells: Engineering and Applications." Biomedicines, vol. 10, No. 2, Jan. 26, 2022, pp. 1-21.
Wang, P. et al. "Research Progress of Chimeric Antigen Receptor T Cell Immunotherapy in Autoimmune Diseases." Chinese Journal of Nephrology, Dialysis & Transplantation, vol. 28, No. 6, Dec. 2019, pp. 550-555, with English abstract.

\* cited by examiner
† cited by third party

*Primary Examiner* — Jeffrey Stucker
*Assistant Examiner* — Brittney E Donoghue
(74) *Attorney, Agent, or Firm* — Fenwick & West LLP

(57) ABSTRACT

The invention provides compositions and methods for suppressing autoimmune components of neurodegenerative diseases and thereby providing therapeutic effects to patients suffering from such diseases. Compositions and methods include immunosuppressive moieties such as regulatory T cells (Tregs) and proteins expressed by Tregs coupled to a chimeric antigen receptor or protein that specifically binds one or more glial cell markers. Therapeutically effective doses of said compounds for treating neurodegenerative diseases including progressive supranuclear palsy (PSP), Parkinson's disease (PD), Alzheimer's, Huntington's disease, amyotrophic lateral sclerosis (ALS), chronic traumatic encephalopathy (CTE), and prion diseases are disclosed.

10 Claims, 6 Drawing Sheets
Specification includes a Sequence Listing.

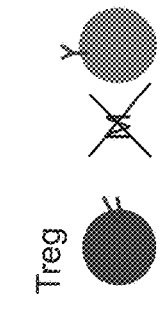
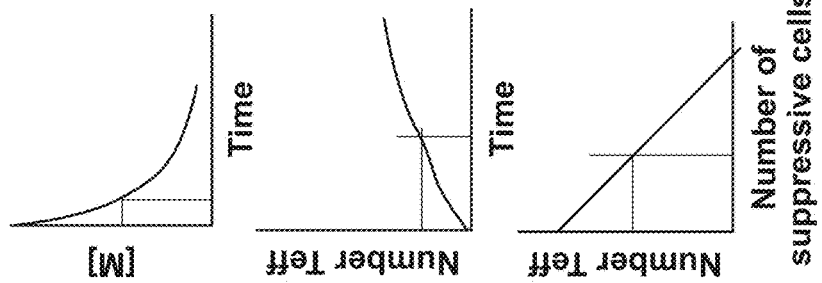
FIG. 6A
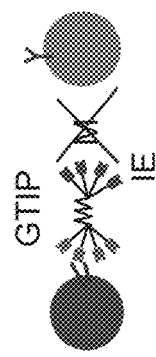
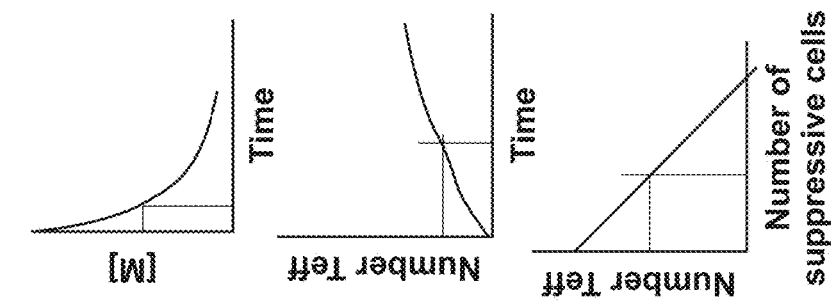
FIG. 6B
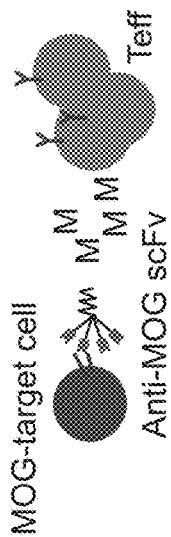
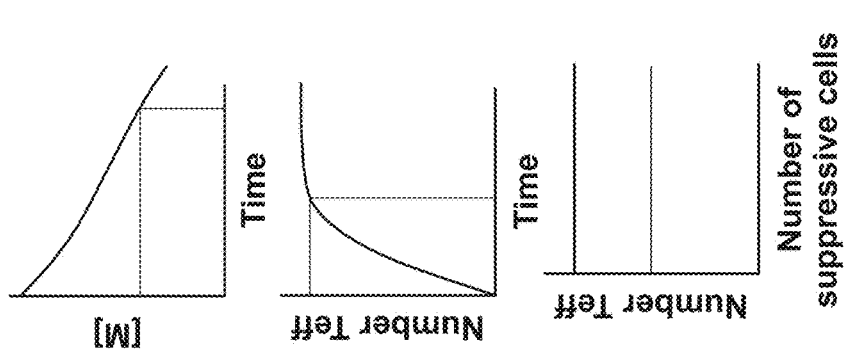
FIG. 6C
FIG. 6D

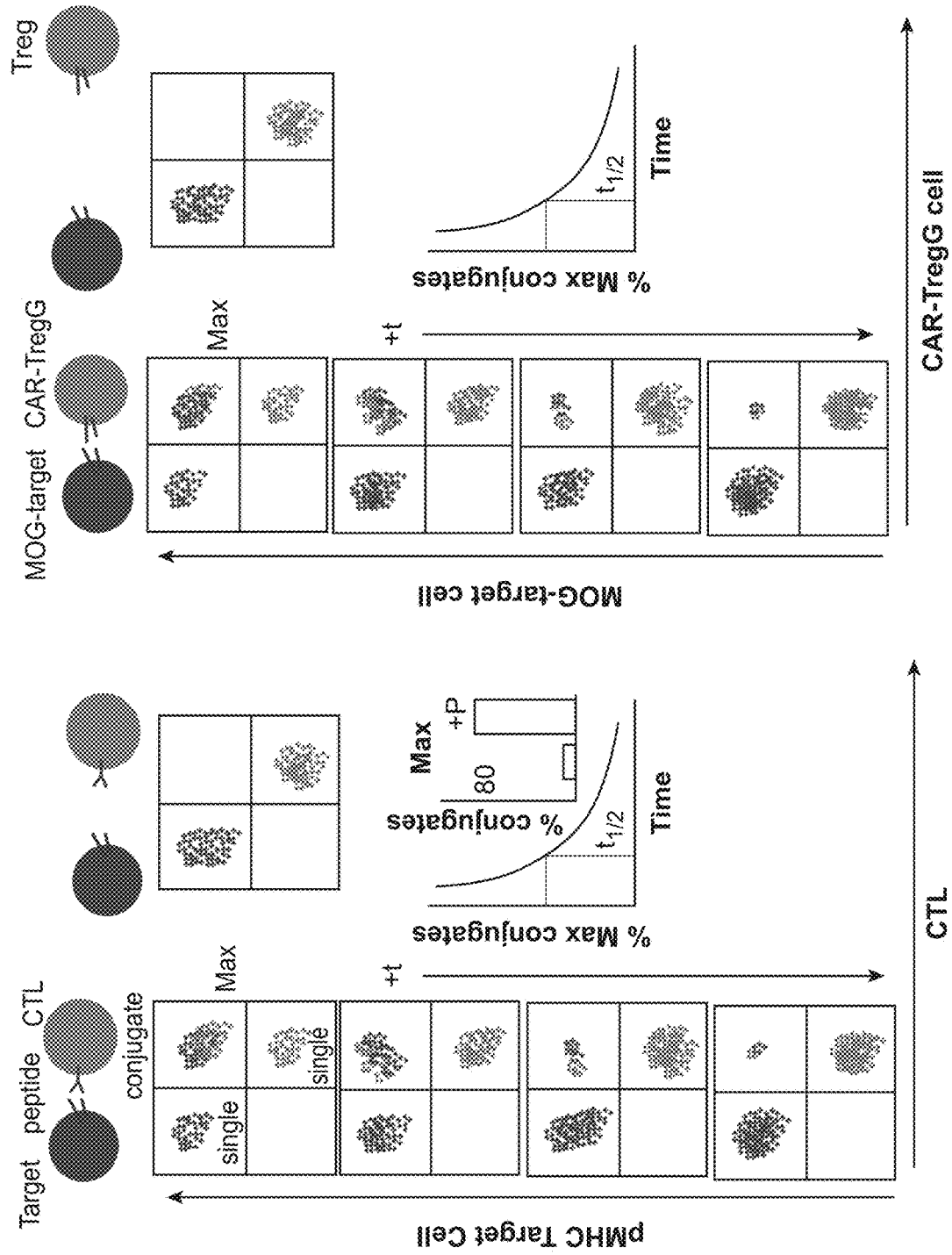

CAR-TREG-BASED THERAPIES FOR TREATING NEURODEGENERATIVE DISEASES

RELATED APPLICATIONS

This application is the National Stage of International Application No. PCT/US2019/023395, filed Mar. 21, 2019, which claims priority to, and the benefit of, U.S. Provisional Application No. 62/648,684, filed Mar. 27, 2018, the content of which is incorporated by reference in its entirety.

SEQUENCE LISTING

The instant application contains a Sequence Listing which has been submitted via Patent Center. Said ASCII copy, created on Jul. 31, 2024, is named 48149US_CRF_sequence listing_31072024.txt, and is 24,883 bytes in size.

FIELD OF THE INVENTION

The invention provides CAR-Treg compositions and methods of use thereof that specifically regulate immune response and inflammation related to various neurodegenerative diseases such as progressive supranuclear palsy and Parkinson's disease.

BACKGROUND

Neurodegenerative diseases such as Parkinson's disease (PD), Alzheimer's disease (AD), Huntington's disease, amyotrophic lateral sclerosis (ALS), and progressive supranuclear palsy (PSP) affect a significant number of people, often resulting in rapid physical and/or mental deterioration and death. There are no known cures for those diseases and treatments focus on managing symptoms and delaying deterioration.

One such disease, PSP, is an idiopathic degenerative disease, not uncommon in the elderly, which mimics Parkinson's disease (PD). The clinical presentation includes the tetrad of supranuclear gaze paralysis, axial rigidity, dementia, and pseudobulbar palsy. It is associated with bradykinesia, severe postural disorder and frequent falls. Pathology is associated with cell loss and Tau neurofibrillary tangles, mainly in the brain stem, globus pallidus, subthalamic nucleus, and dentates nucleus. PSP has a prevalence of 5-6 per 100,000, resulting in 5000-25000 patients per year in the USA. The mean age of onset of the disease is 63 years, with a usual prognosis ranging from 5 to 10 years from diagnosis to death and there are no disease modifying treatments available.

Parkinson's disease is another neurodegenerative disease with no known cure. Parkinson's has a prevalence of about 1-2 per 1,000. Parkinson's is characterized by cell death in the basal ganglia along with astrocyte death and an increase in microglia in the substantia nigra resulting in a dopamine deficiency in those areas. Inclusions called Lewy bodies develop in the damaged cells before cell death. There is speculation regarding the underling mechanisms driving brain cell death in Parkinson's but they remain poorly understood and treatments are current focused on managing the disease symptoms.

SUMMARY

Compositions and methods of the invention use T regulatory lymphocytes (Tregs) or immunosuppressive proteins expressed by Treg cells to modulate neurodegenerative immune responses targeting glial cells in the central nervous system (CNS). By coupling either Tregs or immunosuppressive proteins to a chimeric antigen receptor (CAR) or a single-chain variable fragment (scFv) that specifically recognizes and binds glial cell markers, the immunosuppressive Tregs or proteins are drawn to glial cells of the CNS to reduce inflammation and protect the CNS from autoimmune attack.

The present invention recognizes the lack of effective treatment options for most neurodegenerative diseases and the presence of an autoimmune and/or inflammation component to several such diseases and engineers compositions to specifically suppress those disease components. Compounds and methods of the invention allow glial cells to modulate damaging immune cells such as Type 1 helper cells (Th1), T helper 17 cells (Th17), cytotoxic T cells (CTL), M1 macrophages, and polymorphonuclear neutrophils (PMN).

The present invention directs immunosuppressive molecules (Tregs or immunosuppressive proteins) to oligodendrocyte (ODC) glial cells. The resulting compounds and methods of use thereof recruit the body's own immune system to counter the effects of neurodegenerative diseases such as Parkinson's disease (PD), Alzheimer's disease (AD), Huntington's disease, amyotrophic lateral sclerosis (ALS), and progressive supranuclear palsy (PSP). The invention addresses a mechanism (i.e., autoimmune attack of the central nervous system) by which several neurodegenerative diseases disrupt neural function but does not depend on any particular biochemical causes of the underlying disease. Accordingly, the compounds and methods of the invention can provide therapeutic effects across several neurodegenerative diseases.

Aspects of the invention include methods for treating a neurodegenerative disease in a subject including steps of administering to said subject a therapeutically effective amount of regulatory T cells (Treg) expressing a chimeric antigen receptor (CAR) that specifically binds to a glial cell marker, wherein the neurodegenerative disease is not Multiple Sclerosis (MS). The CAR-Treg then protects neural tissue and reduces inflammation in the neural tissue, thereby treating the neurodegenerative disease. In various embodiments, the subject may be a human.

The glial cell marker may be oligodendrocyte glycoprotein (MOG), oligodendrocyte marker 01 (OM1), oligodendrocyte marker 04 (OM4), neural/glial marker 2 (NG2), A2B5, galactosylceramidase (GALC), myelin basic protein (MBP), glial fibrillary acidic protein (GFAP), or myelin oligodendrocyte specific protein (MOSP). In some embodiments, the glial cell marker is myelin oligodendrocyte glycoprotein (MOG).

The neurodegenerative disease treated may be progressive supranuclear palsy (PSP), Alzheimer's disease (AD), Huntington's disease, Parkinson's disease (PD), amyotrophic lateral sclerosis (ALS), chronic traumatic encephalopathy (CTE), or a prion disease. In some embodiments, the neurodegenerative disease is progressive supranuclear palsy (PSP). In other embodiments, the neurodegenerative disease is Alzheimer's disease (AD). In still other embodiments, the neurodegenerative disease is Parkinson's disease (PD).

In certain aspects, the invention provides a composition comprising an engineered regulatory T cell (Treg) in a therapeutically effective amount to treat a neurodegenerative disease that is not multiple sclerosis, the engineered Treg expressing a chimeric antigen receptor (CAR) that specifically binds to a glial cell marker. The glial cell marker in the composition may be myelin oligodendrocyte glycoprotein (MOG), oligodendrocyte marker 01 (OM1), oligodendrocyte marker 04 (OM4), neural/glial marker 2 (NG2), A2B5, galactosylceramidase (GALC), myelin basic protein (MBP), glial fibrillary acidic protein (GFAP), or myelin oligodendrocyte specific protein (MOSP).

The composition may be therapeutically effective to treat progressive supranuclear palsy (PSP), Parkinson's disease (PD), Alzheimer's, Huntington's disease, amyotrophic lateral sclerosis (ALS), chronic traumatic encephalopathy (CTE), or a prion disease.

Various aspects of the invention include an engineered protein comprising a glial cell-specific binding protein coupled to a molecule expressed by a regulatory T cell (Treg). The molecule expressed by the Treg may be an extracellular immune-suppressive enzyme. In certain embodiments, the molecule expressed by a Treg can be CD73, CD39, indoleamine 2,3-dioxygenase (IDO), or glutamate-oxaloacetate transaminase 1 (GOT1). The glial cell-specific binding protein can be a tetrameric single-chain variable fragment (scFv) of an antibody molecule.

In certain embodiments the Treg-expressed-molecule-bound glial cell-specific binding protein may bind myelin oligodendrocyte glycoprotein (MOG), oligodendrocyte marker 01 (OM1), oligodendrocyte marker 04 (OM4), neural/glial marker 2 (NG2), A2B5, galactosylceramidase (GALC), myelin basic protein (MBP), glial fibrillary acidic protein (GFAP), or myelin oligodendrocyte specific protein (MOSP).

In some aspects, the invention provides an engineered protein comprising a glial cell-specific binding protein coupled to a molecule that mimics the activity of a molecule expressed by a regulatory T cell (Treg). The mimicked molecule expressed by a Treg can be an extracellular immune-suppressive enzyme such as CD73, CD39, indoleamine 2,3-dioxygenase (IDO), or glutamate-oxaloacetate transaminase 1 (GOT1). The mimicked-molecule-bound glial cell-specific binding protein may bind myelin oligodendrocyte glycoprotein (MOG), oligodendrocyte marker 01 (OM1), oligodendrocyte marker 04 (OM4), neural/glial marker 2 (NG2), A2B5, galactosylceramidase (GALC), myelin basic protein (MBP), glial fibrillary acidic protein (GFAP), or myelin oligodendrocyte specific protein (MOSP).

BRIEF DESCRIPTION OF THE DRAWINGS

FIG. 6A illustrates three different cell types tested for suppression of T effector cell proliferation: anti-MOG scFv-bound MOG target cells (left), GTIP-bound MOG target cells (middle), and Tregs (right). FIGS. 6B-6D illustrate a comparison of GTIP-bound MOG target cells (FIG. 6C) to suppress T effector cell proliferation compared to negative (anti-MOG scFV-bound MOG target cells, FIG. 6B) and positive (Tregs, FIG. 6D) controls. The top panel of FIGS. 6B-6D illustrates the concentration of mitogenic metabolite (M) over time following co-culture of one of the cell types from FIG. 6A and M; the middle panel of FIGS. 6B-6D illustrates the number of T effector cells (Teff) over time following co-culture of one of the cell types from FIG. 6A and Teff; the bottom panel of FIGS. 6B-6D illustrates the number of Teff over number of suppressive cells co-cultured together.

FIGS. 7A-7B illustrate the relative avidity of a pMHC for a corresponding cytotoxic T cell clone (FIG. 7A) compared to the relative avidity of a CAR molecule expressing an scFv specific for MOG for a MOG-target cell (FIG. 7B).

FIG. 8 illustrates relative immunoreactivity for seven different scFv proteins against 5 human MOG-1.

DETAILED DESCRIPTION

The invention relates to compositions for regulating autoimmune components of various neurodegenerative diseases. Compositions and methods provided herein target glial-cell-specific markers to draw immunosuppressive molecules (e.g., Tregs or immunosuppressive proteins expressed by Tregs) to the CNS and disrupt autoimmune attacks that contribute to the neurodegenerative effects of diseases such as progressive supranuclear palsy (PSP), Alzheimer's disease (AD), Huntington's disease, Parkinson's disease (PD), amyotrophic lateral sclerosis (ALS), chronic traumatic encephalopathy (CTE), or a prion disease.

The blood-brain barrier can serve as an impediment to treating disorders of the brain or CNS as the barrier can block therapeutic compounds from accessing the affected cells.

Importantly, Tregs are able to cross the blood-brain barrier and can be localized to neurons of the CNS by Treg-bound glial cells, thereby allowing compounds of the invention to effectively treat neurodegenerative disorders of the CNS.

Compounds and methods of the invention do not rely on any disease-specific biochemical mechanisms and instead short circuit the immune response by which many neurodegenerative diseases affect mental and physical deterioration. Accordingly the same compounds and methods may provide therapeutic effects for a number of neurodegenerative diseases.

For example, PSP involves tau protein buildup and neurofibrillary tangles and results in neuron and glial cell damage and loss, associated physical and mental deterioration, and eventual death. Parkinson's disease involves neuron loss in the basal ganglia along with astrocyte death and an increase in microglia in the substantia nigra. Inclusions called Lewy bodies develop in the damaged cells before cell death. ALS is marked by the death of motor neurons in the motor cortex after developing protein-rich inclusions in their cell bodies and axons.

The present invention recognizes that, despite differing underlying causes and disease mechanisms, PSP, Parkinson's, and ALS, along with neurodegenerative diseases including Alzheimer's disease (AD), Huntington's disease, chronic traumatic encephalopathy (CTE), and prion diseases likely include an immune component that contributes to inflammation and CNS degradation. See, Malaspina, et al., 2015, Disease origin and progression in amyotrophic lateral sclerosis: an immunology perspective, International Immunology, 27(3): 117-129; Mosley R, Gendelman H, 2017, T cells and Parkinson's disease, Lancet Neurology, 16(10): 769-71; the contents of each of which are incorporated herein by reference. Accordingly, compounds and methods of the invention, focused on suppressing immune response in the CNS and addressing the chronic inflammation driving many neurodegenerative disease, may be therapeutically effective in treating many those diseases.

Figure 1:
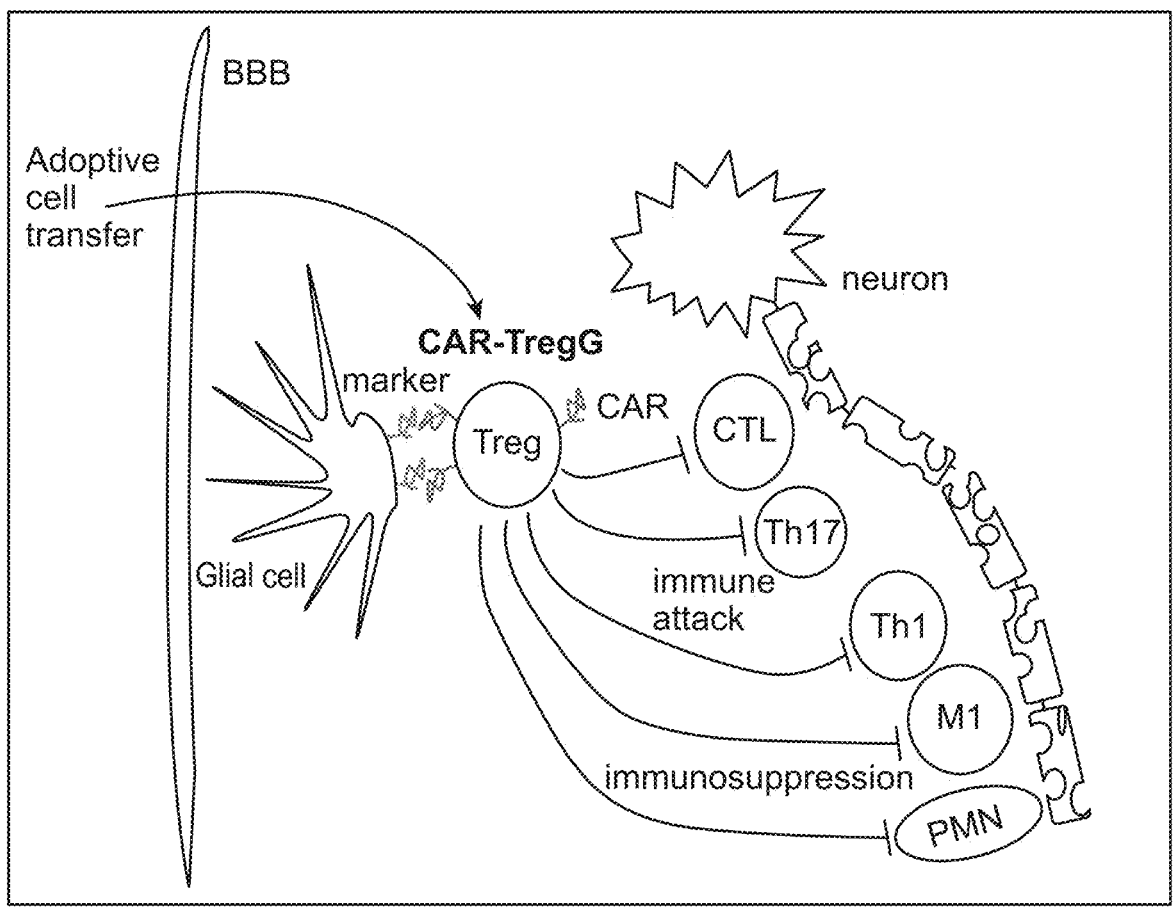
FIG. 1 illustrates a glial-cell-specific CAR-Treg and immunosuppressive function thereof.
Figure 2:
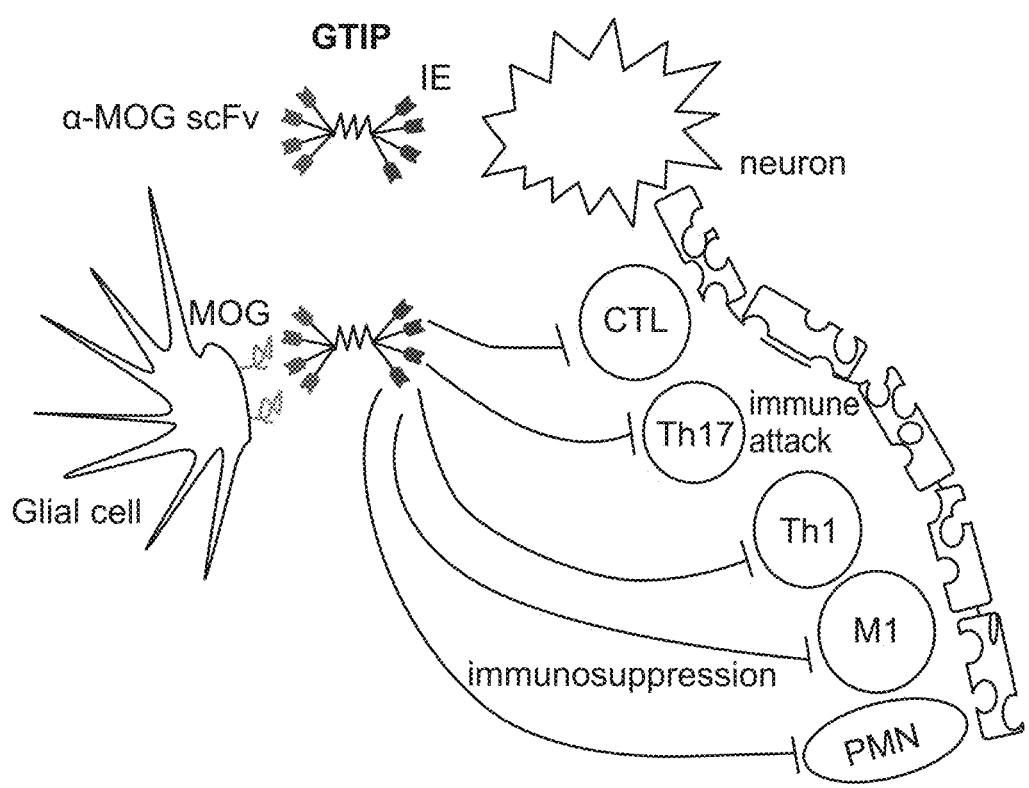
FIG. 2 illustrates a glial-cell-targeted immunosuppressive protein and immunosuppressive function thereof.

Compounds and methods of the invention use chimeric antigen receptors (CAR), antibodies, or single-chain variable fragments (scFv) that specifically bind glial cell markers. The glial cell binding molecules are coupled to a Treg, an immunosuppressive protein expressed by Tregs, or a molecule configured to mimic the immunosuppressive proteins expressed by Tregs. Glial cells are non-neuronal cells that perform a number of functions in supporting neurons in the central and peripheral nervous systems various animals including humans. Glial cells include oligodendrocytes, astrocytes, ependymal cells and microglia. As a result of their functions in maintaining neurons of the CNS, glial cells migrate to neurons of the CNS and can therefore be used to localize therapeutic compounds there. For example, oligodendrocyte (ODC) glial cells traffic to the CNS to maintain axon insulation by creating the myelin sheath. Compounds and methods of the invention include coupling immunosuppressive molecules to glial cells such as ODCs such that, as the glial cells perform their functions, the immunosuppressive molecules are brought into close proximity to the neurons of the CNS as shown in FIGS. 1 and 2. The presence of the immunosuppressive molecules modulates any ongoing immune response and chronic inflammation that may be present in the CNS and contributing to neurodegenerative disease symptoms in PD, PSP, and the like.

Glial-cell-specific targets include proteins expressed by various glial cells and other markers such as myelin oligodendrocyte glycoprotein (MOG), oligodendrocyte marker 01 (OM1), oligodendrocyte marker 04 (OM4), neural/glial marker 2 (NG2), A2B5, galactosylceramidase (GALC), myelin basic protein (MBP), glial fibrillary acidic protein (GFAP), or myelin oligodendrocyte specific protein (MOSP).

In various embodiments, CARs, scFvs, or antibodies can be bound to immunosuppressive molecules and used to target glial cells. CARs are engineered receptors that can provide specificity to immune effector cells (T cells). CARs have been used to confer tumor cell specificity to cytotoxic T lymphocytes for use in cancer immunotherapies. See, Couzin-Frankel, 2013, Cancer immunotherapy, Science, 342 (6165):1432-33; Smith, et al., 2016, Chimeric antigen receptor (CAR) T cell therapy for malignant cancers: Summary and perspective, Journal of Cellular Immunotherapy, 2(2): 59-68; the contents of each of which are incorporated herein by reference. Using similar principles, compounds and methods of the invention include engineering CARs that are specific to markers found on glial cells such as ODCs but, instead of grafting the glial-cell-specific CARs to cytotoxic T cells, they are grafted onto engineered immunosuppressive Tregs.

CAR-Tregs of the invention may express multiple chimeric antigen receptors targeting the same or two or more different glial cell markers.

ScFvs are fusion proteins including variable regions of the heavy (VH) and light chains (VL) of immunoglobulins. ScFvs may be created by cloning VH and VL genes of mice or other animals immunized with the desired target molecule (e.g., MOG). The VH and VL genes can then be expressed in multiple orientations and with various linkers to form a variety of scFvs which may then be experimentally verified to provide desired stability, expression levels, and binding affinity for glial cells or specific markers thereof. ScFvs or antibodies specific to glial cell markers discussed above can be joined to the immunosuppressive proteins discussed below to form fusion proteins capable of providing CNS-localized immunosuppression therapy as shown in FIG. 2 and discussed below.

Antibodies targeting glial cell markers can be produced by methods known in the art including commercially available services for producing custom antibodies from, for example, Pacific Immunology (San Diego, CA) or ABclonal (Woburn, MA).

CAR-Tregs may be engineered by known methods for preparing CAR-T cells. Treg cells may be isolated from a subject, preferably autologous Treg cells from the patient to be treated.

The genes of the Treg cells can then be modified through known techniques such as electroporation, viral vectors, or other forms of transfection with nucleic acids encoding the engineered chimeric antigen receptor of choice. CAR-Treg cells can then be experimentally verified before introduction into the patient's system for treatment.

Regulatory T cells or Tregs modulate the immune system and generally downregulate the induction and proliferation of effector T cells. Tregs prevent auto-immune responses and aid in the discrimination of self and non-self by the immune system. Regulatory T cells produce inhibitory cytokines including Transforming growth factor beta, Interleukin 35, and Interleukin 10 and can induce other cell types to express interleukin-10. Tregs can also produce Granzyme B, which in turn can induce apoptosis of effector cells. Tregs also function through reverse signaling through direct interaction with dendritic cells and the induction of immunosuppressive indoleamine 2,3-dioxygenase. Tregs can also downregulate immune response through the ectoenzymes CD39 and CD73 with the production of immunosuppressive adenosine. Tregs also suppress immune response through direct interactions with dendritic cells by LAG3 and by TIGIT. Another control mechanism is through the IL-2 feedback loop. Another mechanism of immune suppression by Tregs is through the prevention of co-stimulation through CD28 on effector T cells by the action of the molecule CTLA-4.

FIG. 1 illustrates a CAR-Treg targeting glial cells and its therapeutic mechanism. The CAR-Treg cell expresses CARs that specifically bind markers on the glial cell. The CAR-Treg cell is thereby bound to the glial cell and carried across the blood-brain barrier and localized to neurons of the CNS through the natural function of the glial cell. The bound Treg cell then performs its natural regulatory function by suppressing immune attack of the local neurons.

FIG. 2 shows a glial-cell-targeted immunosuppressive protein (GTIP) of the invention suppressing an immune attack of a neuron. GTIPs may comprise an immunosuppressive protein or enzyme present in Treg cells such as extracellular enzymes that scavenge immune activating metabolites (e.g., ATP, AMP, tryptophan, and glutamate). Such extracellular enzymes may include CD73, CD39, indoleamine 2,3-dioxygenase (IDO), and glutamate-oxaloacetate transaminase 1 (GOT1). In FIG. 2, a glial cell expressing MOG is bound by a GTIP consisting of an anti-MOG scFV linked to an immunosuppressive enzyme (IE). The glial cell, in performing its neuron-related functions, localizes the bound IE to a neuron undergoing immune attack by various immune cells (Th17 cells, Th1 cells, CTL cells, M1 cells, and PMN cells) and modulates or shuts down the immune response, thereby preserving the neuron and reducing the symptoms of the underlying neurodegenerative disease. GTIPs may be useful in treating neurodegenerative diseases such as progressive supranuclear palsy (PSP), Alzheimer's disease (AD), Huntington's disease, Parkinson's disease (PD), amyotrophic lateral sclerosis (ALS), chronic traumatic encephalopathy (CTE), multiple sclerosis (MS), and a prion disease.

GTIPs of the invention may include one or more immunosuppressive proteins (including two or more different proteins) linked to one or more scFVs or antibodies targeting the same or two or more different glial cell markers. Proteins can be joined by any known means to form GTIPs of the invention including, for example, fusion proteins or biotin-streptavidin linkage.

Adoptive cell transfer techniques as used in cancer immunotherapy techniques including those involving cytotoxic T lymphocytes may be used to prepare autologous CAR-Tregs for use in compounds and methods of the invention. See, Rosenberg, et al., 2008, Adoptive cell transfer: a clinical path to effective cancer immunotherapy, Nat Rev Cancer, 8(4):299-308, the contents of which are incorporated herein by reference.

A CAR-Treg or glial-cell-targeted immunosuppressive protein of the invention may be incorporated into carrier systems containing one or more of the therapeutic compounds described herein. In certain embodiments, the carrier system can be a nanoparticle that includes disulfide-cross-linked polyethyleneimine (CLPEI) and a lipid. The lipid may be a bile acid, such as cholic acid, deoxycholic acid, and lithocholic acid. Such carrier systems are described further in the Examples below. Other exemplary carrier systems are described for example in Wittrup et al. (Nature Reviews/Genetics, 16:543-552, 2015), the content of which is incorporated by reference herein in its entirety.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient, i.e., at least one a therapeutic compound of the invention and/or derivative thereof, in combination with a pharmaceutically acceptable carrier.

The effective dosage of each agent can readily be determined by the skilled person, having regard to typical factors each as the age, weight, sex and clinical history of the patient. In general, a suitable daily dose of a compound of the invention will be that amount of the compound which is the lowest dose effective to produce a therapeutic effect. Such an effective dose will generally depend upon the factors described above.

If desired, the effective daily dose of the active compound may be administered as two, three, four, five, six or more sub-doses administered separately at appropriate intervals throughout the day, optionally, in unit dosage forms.

The pharmaceutical compositions of the invention include a "therapeutically effective amount" or a "prophylactically effective amount" of one or more of the compounds of the present invention, or functional derivatives thereof. An "effective amount" is the amount as defined herein in the definition section and refers to an amount effective, at dosages and for periods of time necessary, to achieve the desired therapeutic result, e.g., a diminishment or prevention of effects associated with neuropathic and/or inflammatory pain. A therapeutically effective amount of a compound of the present invention or functional derivatives thereof may vary according to factors such as the disease state, age, sex, and weight of the subject, and the ability of the therapeutic compound to elicit a desired response in the subject. A therapeutically effective amount is also one in which any toxic or detrimental effects of the therapeutic agent are outweighed by the therapeutically beneficial effects.

A "prophylactically effective amount" refers to an amount effective, at dosages and for periods of time necessary, to achieve the desired prophylactic result. Typically, since a prophylactic dose is used in subjects prior to, or at an earlier stage of disease, the prophylactically effective amount may be less than the therapeutically effective amount. A prophylactically or therapeutically effective amount is also one in which any toxic or detrimental effects of the compound are outweighed by the beneficial effects.

Dosage regimens may be adjusted to provide the optimum desired response (e.g. a therapeutic or prophylactic response). For example, a single bolus may be administered, several divided doses may be administered over time or the dose may be proportionally reduced or increased as indicated by the exigency of the therapeutic situation. It is especially advantageous to formulate parenteral compositions in dosage unit form for ease of administration and uniformity of dosage. Actual dosage levels of the active ingredients in the pharmaceutical compositions of this invention may be varied so as to obtain an amount of the active ingredient which is effective to achieve the desired therapeutic response for a particular subject, composition, and mode of administration, without being toxic to the patient.

The term "dosage unit" as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the compound, and (b) the limitations inherent in the art of compounding such an active compound for the treatment of sensitivity in individuals.

In some embodiments, therapeutically effective amount can be estimated initially either in cell culture assays or in animal models, usually mice, rabbits, dogs, or pigs. The animal model is also used to achieve a desirable concentration range and route of administration. Such information can then be used to determine useful doses and routes for administration in other subjects. Generally, the therapeutically effective amount is sufficient to reduce or inhibit neuropathic and/or inflammatory pain in a subject. In some embodiments, the therapeutically effective amount is sufficient to eliminate neuropathic and/or inflammatory pain in a subject.

Dosages for a particular patient can be determined by one of ordinary skill in the art using conventional considerations, (e.g. by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the compounds of the invention or functional derivatives thereof, and the condition of the patient, as well as the body weight or surface area of the patient to be treated. The size of the dose is also determined by the existence, nature, and extent of any adverse side-effects that accompany the administration of a particular vector, formulation, or the like in a particular subject. Therapeutic compositions comprising one or more compounds of the invention or functional derivatives thereof are optionally tested in one or more appropriate in vitro and/or in vivo animal models of disease, such as models of neuropathic and/or inflammatory pain, to confirm efficacy, tissue metabolism, and to estimate dosages, according to methods well known in the art. In particular, dosages can be initially determined by activity, stability or other suitable measures of treatment vs. non-treatment (e.g., comparison of treated vs. untreated cells or animal models), in a relevant assay. Formulations are administered at a rate determined by the LD50 of the relevant formulation, and/or observation of any side-effects of compounds of the invention or functional derivatives thereof at various concentrations, e.g., as applied to the mass and overall health of the patient. Administration can be accomplished via single or divided doses.

Administering typically involves administering pharmaceutically acceptable dosage forms, which means dosage forms of compounds described herein, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition, which is hereby incorporated by reference in its entirety. Administering may be carried out orally, intradermally, intramuscularly, intraperitoneally, intravenously, subcutaneously, or intranasally. Compounds may be administered alone or with suitable pharmaceutical carriers, and can be in solid or liquid form, such as tablets, capsules, powders, solutions, suspensions, or emulsions.

A pharmaceutical composition containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from sweetening agents, flavoring agents, coloring agents and preserving agents, in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108, 4,166,452 and 4,265,874 (the contents of each of which is incorporated by reference herein in its entirety), to form osmotic therapeutic tablets for control release.

Formulations for oral use may also be presented as hard gelatin capsules in which the active ingredient is mixed with an inert solid diluent, for example calcium carbonate, calcium phosphate or kaolin, or as soft gelatin capsules wherein the active ingredient is mixed with water or an oil medium, for example peanut oil, liquid paraffin or olive oil.

Formulations may also include complexes of the parent (unionized) compounds with derivatives of β-cyclodextrin, especially hydroxypropyl-β-cyclodextrin.

An alternative oral formulation can be achieved using a controlled-release formulation, where the compound is encapsulated in an enteric coating.

Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate, polyvinyl-pyrrolidone, gum tragacanth and gum acacia; dispersing or wetting agents such as a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents which have been mentioned above. The sterile injectable preparation may also be in a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Each active agent may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions are suitable. Topical application includes the use of mouth washes and gargles.

The term "pharmaceutical composition" means a composition comprising a compound as described herein and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms.

The term "pharmaceutically acceptable carrier" is used to mean any carrier, diluent, adjuvant, excipient, or vehicle, as described herein. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgment, suitable for use in contact with the cells of humans and lower animals without undue toxicity, irritation, allergic response, and the like, and are commensurate with a reasonable benefit/risk ratio.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

EXAMPLES

Example 1

Study Design

Participants with Progressive Supranuclear Palsy (PSP) will receive a single infusion of ex vivo-expanded autologous CD4+CD127lo/−CD25+ CAR-T regulatory cells (Tregs). CAR-Tregs will be designed to specifically recognize myelin-oligodendrocyte protein (MOG), a glycoprotein specifically expressed in the central nervous system (CNS), and induce immune tolerance and anti-inflammatory effects in the brain.

The primary objective will be to assess the safety and feasibility of intravenous infusion of ex vivo-selected, expanded and transduced autologous CNS-specific CAR-Tregs in at least 5 patients with PSP.

Primary outcome measures will be:
1. adverse events
2. laboratory abnormalities
3. infusion reactions
4. complications related to infection
5. potential negative impact on the course of PSP The secondary objective will be to assess the effect of CNS-specific CAR-Tregs on PSP and obtain indication on the potential application in other neurodegenerative diseases. The end points will be:
1. Assess the effect of CNS-specific CAR-Tregs on clinical, neuropsychological, radiological and biomechanical parameters in PSP patients.
2. Obtain indication on the potential therapeutic usage of CNS-specific CAR-Tregs in other neurodegenerative diseases, including Alzheimer's disease (AD).
3. Obtain indication on a potential phase-II randomized, double-blind, placebo-controlled trial that may provide valuable insights into the potential efficacy of CAR-Tregs for neurodegenerative disorders.

Patient Assessment

Clinical and neuropsychological assessment: A detailed description of the inclusion and exclusion criteria, and clinical (motor and neuropsychological) and neuroimaging assessments will be performed as previously reported (Giordano et al., J. Transl. Med. 2014; Canesi et al., J. Transl. Med. 2016, incorporated herein by reference). The patients will undergo neurological examinations to assess motor function using the following scales: unified Parkinson's disease rating scale (UPDRS part-III, motor score), Hoehn and Yahr staging (H&Y), PSP rating scale (PSP-RS) (Goetz et al., Mov. Disord. 2004; Golbe et al., Brain 2007; the contents of each of which are incorporated herein by reference). Mini mental state evaluation (MMSE) will be also performed as previously described (Folstein et al. J. Psychiatr. Res. 1975, incorporated herein by reference). All these tests will be assessed at baseline and at each follow-up point (1, 3, 6 and 12 months after cell administration). The clinical conditions will be classified as "stable" if the UPDRS and PSP-RS scores did not diminish by more than 30% compared to baseline and the H&Y staging did not change at the defined time point (Canesi et al., J. Transl. Med. 2016, incorporated herein by reference).

Neuroimaging: All patients will undergo longitudinal neuroimaging assessments, using brain magnetic resonance imaging (MRI) (baseline, 24 h after cell administration and after 1 year), striatal dopamine transporter single photon emission computed tomography (SPECT) and positron emission tomography (PET) (both at baseline and after 12 months). Tropanic tracers labeled with Iodine-123 (FP-CIT) and 18F-Fluoro-2-deoxyglucose (Beta-CIT) will be used for SPECT imaging and for PET/TC imaging, respectively.

For SPECT, intravenous administration of 110-140 MBq of [123I] FP-CIT (Datscan, GE-Health, Amersham, UK) will be performed 30-40 min after thyroid blockade (10-15 mg of Lugol solution per os) in all patients. The analysis will be performed as previously described (Isaias et al., NeuroReport 2007, incorporated herein by reference). A volumetric template of grey matter anatomic distribution will be generated from the Montreal Neurological Institute MRI single participant brain atlas by applying a macroscopic anatomical method (automated anatomic labeling), and will be reoriented and reformatted to obtain a 2.64-cm thick reference section. A template of eight irregular regions of interest (ROIs) will be manually drawn on this section to assess the anatomical extent of striatal and occipital structures having both specific and nonspecific uptake of [123 I] FP-CIT, respectively. The ROI template will be also positioned on the reference SPECT section and adjusted on both striatal and occipital cortex. Striatal ROIs will be also segmented into their anterior (caudate nucleus) and posterior (putamen) portions.

Specific striatal dopamine uptake transporter (DAT) binding of [123 I] FP-CIT will be calculated in the whole striatum, putamen and caudate nucleus using the formula: [(mean counts in specific ROI)-(mean counts in occipital ROI)]/(mean counts in occipital ROI). Putamen/caudate ratios for each subject will also be calculated.

All patients will also undergo F-Fluoro-2-deoxyglucose positron emission tomography scanning (FDGPET) at rest, after intravenous injection of 170 MBq. Each acquisition will include a computed tomography (CT) transmission scan of the head (50 mAs lasting 16 s) followed by a three dimensional (3D) static emission of 15 min using a Biograph Truepoint 64 PET/CT scanner (Siemens). PET sections will be reconstructed using an iterative algorithm (OSEM), corrected for scatter and for attenuation, using density coefficients derived from the low dose CT scan of the head obtained with the same scanner. Images will be reconstructed in the form of transaxial images of 128 A~128 pixels of 2 mm, using an iterative algorithm, ordered-subset expectation maximization (OSEM). The resolution of the PET system will be 4-5 mm FWHM.

Biomechanical evaluation: Biomechanical evaluation will be assessed at baseline and at six and 12 months after CAR-Treg cell administration. Two specific sets of parameters, one for standing and one for gait initiation, will be automatically extracted by means of ad hoc algorithms (Carpinella et al., IEEE Trans Neural Syst Rehabil Eng. 2007, incorporated herein by reference). For standing, the center of pressure (CoP) mean velocity and spatial displacement will be measured (Canesi et al., J. Transl. Med. 2016, incorporated herein by reference). To examine gait initiation, anticipatory postural adjustment will be analyzed (Canesi et al., J. Transl. Med. 2016, incorporated herein by reference) (i.e. imbalance and unloading phases) and measure the following parameters: (1) the duration of both phases, (2) the antero-posterior (AP) and mediolateral (ML) shift and velocity of the CoP, (3) the CoP mean length and velocity. The (4) length and (5) velocity of the first step will also be measured. Spatial parameters will be normalized on the basis of body height (% BH).

Preparation and Administration of CAR-Treg Cells

Treg isolation and expansion: PolyTregs will be selected and expanded from five individuals with PSP based on three cell surface markers-CD4, CD25, and CD127-to purify the FOXP3+ Tregs present in the peripheral blood as described previously (Putnam et al., Diabetes 2009; Bluestone et al., Sci. Transl. Med., 2015, incorporated herein by reference).

400 ml of fresh peripheral blood will be collected into blood pack units containing citrate phosphate dextrose and processed within 24 hours for isolation of PBMCs via Ficoll density gradient. Tregs will be isolated on a high-speed cell sorter with the following GMP-grade lyophilized antibodies: CD4-PerCP (peridinin chlorophyll protein) (L200 clone), CD127-PE (phycoerythrin) (40131 clone), and CD25-APC (allophycocyanin) (2A3 clone). The sorted CD4+CD127lo/−CD25+ cells will be collected into 3 ml of X-VIVO 15 medium (Lonza, catalog no. 04-418Q) containing 10% human heat-inactivated pooled AB serum (Valley Biomedical). Tregs will be analyzed for purity after sorting. The expected purity of CD4+CD127lo/−CD25+ cells is more than 96% (Bluestone et al., Sci. Transl. Med., 2015, incorporated herein by reference).

Purified Tregs will be cultured with clinical-grade Dynabeads coated with anti-CD3 and anti-CD28 plus recombinant IL-2 as previously described (Bluestone et al., Sci. Transl. Med., 2015, incorporated herein by reference). A unit of blood is expected to yield between $4.2 \times 10^6$ and $11.8 \times 10^6$ purified CD4+CD127lo/−CD25+ Tregs, (Bluestone et al., Sci. Transl. Med., 2015, incorporated herein by reference). The expanded Treg preparations are expected to be around 90% FOXP3+. Treg preparations will be checked for viability, CD4+ percentage, and CDS+ cell contamination (Bluestone et al., Sci. Transl. Med., 2015, incorporated herein by reference).

Phenotypic and TCR analysis of expanded polyTregs: Key cell surface markers, CD4 and CD 127, used to isolate the Tregs, will be checked after expansion.

Previous data have shown that the naive CD45RA+ Tregs preferentially expand in these cultures and CD45RA+RO− cells down-regulate CD45RA and up-regulate CD45RO over the expansion period (Bluestone et al., Sci. Transl. Med., 2015, incorporated herein by reference). CCR7, a Treg trafficking receptor, CD38, a multifunctional ectoenzyme associated with enhanced Treg function and CD45 RO will be determined before and after expansion. The TCRB repertoire of the expanded Tregs will be also analyzed and compared to the freshly isolated populations to determine the polyclonality of the expanded Tregs. The expanded cells are expected to exhibit polyclonality indistinguishable from the preexpansion cultures and that the Tregs remain a highly diverse population after expansion (Bluestone et al., Sci. Transl. Med., 2015, incorporated herein by reference).

Functional analysis of expanded polyTregs: The following assays will be performed after Treg expansion (Bluestone et al., Sci. Transl. Med., 2015, incorporated herein by reference):

DNA methylation state of enhancer region of the FOXP3 locus to assess the overall purity and stability of expanded Tregs.

Cytokine production (IFNy, IL-4. IL-5 and IL-17) to assess lymphocyte phenotype.

In vitro suppressive activity to determine the functional potential of expanded cells.

Production and functional analysis of CAR-Treg cells: CAR RNA will be optimized for anti-MOG CAR expression on Tregs after electroporation of human Tregs and on mouse Tregs after adoptive transfer to PSP mouse models as per published protocols (Zhao, Yet al., 2010 Cancer Res and Beatty, G L et al., 2014 Cancer Immunol Res; Singh, N et al., 2014 Oncoimmunol; the contents of each of which are incorporated herein by reference). Delivery of anti-MOG CAR using second-generation lentivirus vectors and standard protocols (Levine, B. L. et al., 2017 Mol Ther Methods & Clin Dev, incorporated herein by reference) will also be optimized. Human Tregs will be either transduced under GMP condition using electroporation of RNA (about 1 $\mu g/3 \times 10^6$ Treg) or by lentivirus transduction ($1 \times 10^6$ pfu/$3 \times 10^6$ Treg). Clinical grade RNA for anti-MOG CAR will be produced. About 0.9 mg RNA per patient for $2.6 \times 10^9$ Treg cells; 4.5 mg for 5 patients will be required. Clinical grade lentivirus will be produced. About $8.7 \times 10^9$ pfu per patient for $2.6 \times 10^9$ Treg cells; $4.3 \times 10^{10}$ pfu for 5 patients will be required. Functional analysis of MOG-specific CAR-Tregs will be performed as described above in 3.3.

Cell Administration

One single administration of MOG-specific CAR-Tregs will be performed for each patient ($2.6 \times 10^9$ CAR-Tregs per patient). Cells will be administered to at least 5 PSP patients. Patients will receive premedication with acetaminophen and diphenhydramine. CAR-Tregs will be infused via a peripheral intravenous line over 10 to 30 min. Vital signs will be taken before and after infusion, then every 15 min for at least 1 hour, then every hour for the first 4 hours, and every 4 hours for 20 hours. Chemistries and complete blood count with differential blood count will be repeated the next day before discharge from the clinical research unit. Patients will be seen for follow-up assessments on day 4 after infusion, then weekly for 4 weeks, then every 13 weeks for 1 year, and then every 26 weeks for 2 years. Telephone monitoring for adverse events will continue every 6 months for 5 years after infusion followed by a final clinic visit.

Patient assessment after CAR-Treg cell infusion The effect of CNS-specific CAR-Tregs on clinical, neuropsychological, radiological and biomechanical parameters in PSP patients will be assessed as described above. All the tests will be performed at each follow-up point: 1, 3, 6 and 12 months after cell administration.

Example 2

Drugs for Multiple Sclerosis (MS) that exploit components of immunosuppressive T regulatory lymphocytes (Tregs) to shut down the damaging immune responses that cause disease will be developed and tested. The worldwide MS market is about $21.5 billion but the approved drugs for the most common form of MS give only modest disease modification with significant side effects. For more severe forms of MS the treatment options are limited to only 1 recently approved drug.

There are 11 FDA approved drugs for Relapsing Remitting form of MS (RRMS-85% of diagnosed MS). There are several orally available and antibody based drugs currently approved or under clinical evaluation for RRMS. In March 2017 the FDA approved the use of Ocrelizumab (anti-CD20 antibody, Roche) for Primary Progressive MS (PPMS—about 10% of diagnosed MS). Ocrelizumab gave a 25% reduction in symptoms and is at present the only immunomodulatory for PPMS in the USA. Secondary Progressive MS (SPMS) invariably develops in patients with RRMS, for which there are also limited disease modification options.

Production of Biologics

Anti-MOG hybridomas will be produced by immunization of mice with recombinant human MOG through CROs. VH and VL genes will be cloned and anti-scFv molecules. The orientation of VH and VL as well as the linkers (between the scFv or inside each scFv) may greatly affect the stability, expression level and binding ability of GTIP. In some cases, only one of these forms will produce functional molecules. Therefore, several orientations of VH-VL will be expressed on a small scale and tested before scale-up production. An expression construct will be generated encoding 4 anti-MOG scFv with connecting linkers, a central linker, then connecting to Treg-associated enzymes or mimetics.

Validation of GTIP Protein Products in Mouse MS Models

GTIPs will be tested in mouse, acute and chronic EAE models of MS. The levels of Th1, Th17, CTL (blood and CNS) specific for myelin basic protein (MBP), myeloid inflammatory cells (macrophages and neutrophils) and anti-MBP antibodies will be measured. Immunological responses will be correlated with disease progression. Dosing will be varied to gain insights into potential use in late stage MS. Products will be dosed in normal mice to gain insights into any potential off target effects.

Clinical Evaluation.

Clinical studies will be conducted to test the efficacy the GTIPs as disease modifying agents in MS. The products will first be tested be in RRMS patients who are unresponsive to first use drugs. Safety and tolerability will be measured using dosing regimes similar to those for antibody therapies (e.g. first 3 i.v. doses every 2 weeks then every 4 weeks for 20 weeks). In phase 2 studies, primary measures will be decreased disease relapse frequency and brain lesions. Secondary measures will be decreased inflammatory cytokines, Th1/Th17 cells and other leukocytes levels in the blood. Side effects may include increases susceptibility to infection.

These studies will allow us to benchmark the effectiveness of the compounds against other second use drugs that give up to 49% reduction in relapse frequency. If the products show acceptable levels of efficacy then they will be entered into the longer-term clinical phase 2 studies in PPMS patients. Primary measures will be delayed decline in motor function and reduced brain lesions and secondary measures will be reduced levels of inflammatory cytokines, Th1/Th17 cells and other leukocytes in the blood.

Example 3

Figure 3:
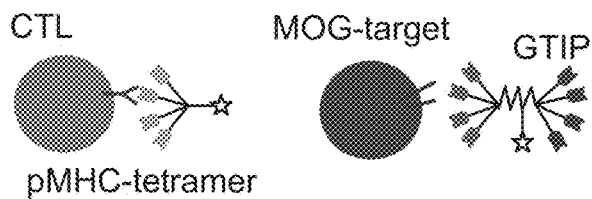
FIG. 3 illustrates binding of a pMHC-tetramer to a cytotoxic T cell and binding of GITPs of the invention to a target MOG protein.
Figure 4A:
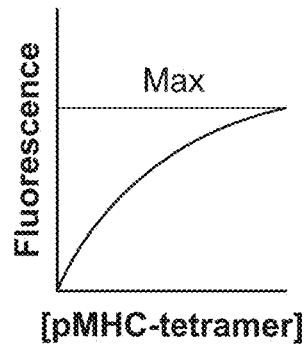
FIGS. 4A-4B illustrate maximum staining of MOG target cells with labeled GITP protein (FIG. 4B) compared with that of CTL and pMHC (FIG. 4A).
Figure 4B:
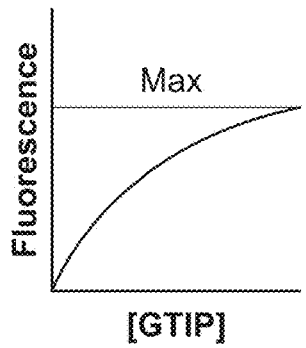
Figure 5A:
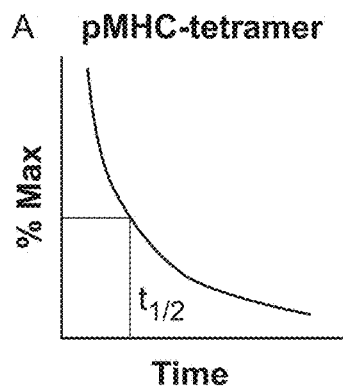
FIGS. 5A-5B illustrate half-life of staining of MOG target cells with labeled GITP protein (FIG. 5B) compared with that of CTL and pMHC (FIG. 5A).
Figure 5B:
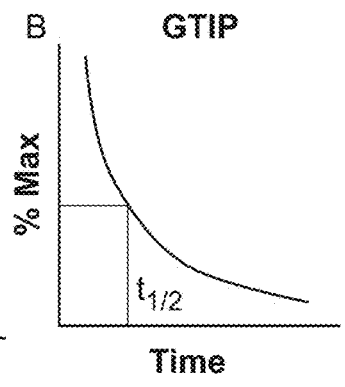

Tetramer binding assays will be used to compare the avidity of GITP binding to target cells with that of known tetramers against T cells (Ober, B et al., 2000 Int Immunol, incorporated herein by reference) as shown in FIG. 3. The relative avidity of H-Y peptide/MHC H-2Db (pMHC) tetramer for TCR on B6.2.16 CTL will be measured by determining two parameters using cell staining and flow-cytometry (FCM). These will be the concentration required to give maximum staining and the half-life (t1/2) of tetramer staining (after cell washing). MOG-target cells will be produced by gene transfection of non-adherent target cells (e.g. RMA or Jurkat cells). Antibody staining and flow-cytometry (FCM) will confirm the surface expression of MOG. Antibody staining and FCM will identify transfectants with the same MOG levels as the B6.2.16 TCR on CTL. The maximum staining and half-life of staining of MOG target cells with labeled GITP protein will be measured and compared with that of CTL and pMHC tetramer as shown in FIGS. 4 and 5. The aim will be to produce GITP that have avidities of cell interactions comparable or better that that of CTL and pMHC tetramers. If tetrameric anti-MOG scFv in GITP molecules falls short of this bar the valances of scFv can be increased. If even higher valences are required, nanoparticle scaffolds may be used to achieve the necessary avidity for target cell binding.

Example 4

The ability of GTIP bound to MOG-target cells to suppress the proliferation of T effector (T eff) cells will be tested. GTIP composed of a tetramer of a given scavenger IE (see table 1 below) will be bound to MOG-target cells, washed then incubated with proliferating human Teff (generated using standard procedures e.g. 3 days after anti-CD3/CD28 and IL-2 stimulation) (FIG. 6C).

TABLE 1

| Metabolite (M) | Immuno-suppressive scavenging enzyme (IE) |
|---|---|
| AMP | CD73 |
| ATP | CD39 |
| TRP | IDO |
| GLU | GOT |

Cells will be cultured in medium spiked with the relevant mitogenic metabolite (M) that is the substrate of the IE in the GTIP (see table above). Over time the concentration of M and the number of Teff will be measured as shown in FIGS. 6B-6D. The number of GTIP—decorated, MOG-target cells will be titrated against the number of Teff after a fixed time to give an index of suppressive activity. Negative control experiments (FIG. 6B) in which just tetrameric scFv bound to MOG-target cell will result on longer M half-lives, greater amounts of Teff after a fixed time and no suppressive activity on Teff cell accumulation. As a positive control (FIG. 6D) human Tregs (generated under standard conditions e.g. 9 days after CD3/CD28 and TGF-β stimulation) will be co-cultured with Teff cells and the suppressive activity compared to that of GTIP-decorated, MOG-target cells. Comparable efficacy on a cell-to-cell basis of GTIP—decorated, MOG-target cells with that of human Treg cells will serve as positive validation of a GTIP molecule with a particular IE. The assays will identify GTIP composed of the most effective IE molecule. Efficacy may be increased by adding more than one type of IE molecules in a GTIP molecule and/or increasing the valancy of IE molecules.

Example 5

An assay will be used to measure the ability of CAR molecules expressing scFv specific for MOG to bind Treg cells to MOG-expressing target cells with a relative avidity approximating that of a physiologically meaningful T cell: target cell interaction. The physiologically meaningful T cell: target cell interaction used for comparison is a CTL: peptide/MHC(pMHC)/target cell interaction. This will be done using a flow cytometry (FCM)-based assay for cell-cell conjugates (Opferman, J T et al., 2001 Int Immunol., incorporated herein by reference).

The relative avidity of pMHC target for the relevant CTL clone (B6.2.16) will be determined (FIG. 7A). Targets will be labeled with the vital dye PKH26 (black) and CTL with CFSE (gray), co-incubated for 4 hours then subjected to a standard shear force and examined by FCM. Conjugates will be detected as double staining doublets and will depend on the presence of H-Y peptide antigen. The relative avidity of pMHC target: B6.2.16 CTL interaction will be measured by two parameters—the maximum level of conjugate formation (about 80% of total input cells) and the half-life of dissociation of conjugates. MOG-target cells will be incubated with CAR-anti-MOG scFv expressing human T cells generated under standard conditions (e.g. lentivirus transduction of anti-CD3/CD28 IL-2 stimulated T cells) (FIG. 7B). The half-life of conjugates between labeled cells will be measured by FCM (right column of FIGS. 7A-B). Comparable conjugate half-life with that of a CTL:pMHC/target cell will indicate a physiological avidity of anti-MOG scFv/CAR on T cell for MOG-positive targets cells.

Example 6

ScFv antibodies were generated specific to human MOG by affinity panning of a human phage display scFv library. QC SDS-PAGE was conducted before library screening to assess purity of the target. In order to reduce non-specific binders, pre-counter selections were performed using polystyrene flat bottom plates and a blocking buffer against the phage library first before targeting screening.

After three rounds of biopanning, positive enriching was observed. 20 clones were randomly picked from the third round and QC monoclonal phage ELISA was conducted. 18 clones were found to bind to the target compared to the control. All 18 positive clones were sequenced.

Another 20 clones were picked from the third round and subjected to QC monoclonal phage ELISA. All 20 of the second set of clones were found to bind to the target compared to the control. All of them were sequenced.

After analysis of the 38 positive clones, 7 positive clones (clone 1, 3, 6, 10, 13, 17, 21) with unique sequence were identified. The sequences of the 7 scFv proteins and the DNA sequences encoding them are listed below:

Clone 1 DNA (SEQ ID NO. 1):
GAGGTGCAGCTGTTGGAGTCTGGGGGAGGCTTGGTACAGCCTGGGGGGTCCCTGAG

ACTCTCCTGTGCAGCCTCTGGATTCACCTTTAGCAGCTATGCCATGAGCTGGGTCCG

CCAGGCTCCAGGGAAGGGGCTGGAGTGGGTCTCAAGTATTTCTGATTATGGTAATAC

TACAGCTTACGCAGACTCCGTGAAGGGCCGGTTCACCATCTCCAGAGACAATTCCAA

GAACACGCTGTATCTGCAAATGAACAGCCTGAGAGCCGAGGACACGGCCGTATATT

ACTGTGCGAAAAATGCTAATTATTTTGACTACTGGGGCCAGGGAACCCTGGTCACCG

TCTCGAGCGGTGGAGGCGGTTCAGGCGGAGGTGGCAGCGGCGGTGGCGGGTCGACG

GACATCCAGATGACCCAGTCTCCATCCTCCCTGTCTGCATCTGTAGGAGACAGAGTC

ACCATCACTTGCCGGGCAAGTCAGAGCATTAGCAGCTATTTAAATTGGTATCAGCAG

AAACCAGGGAAAGCCCCTAAGCTCCTGATCTATGATGCATCCAGTTTGCAAAGTGG

GGTCCCATCAAGGTTCAGTGGCAGTGGATCTGGGACAGATTTCACTCTCACCATCAG

CAGTCTGCAACCTGAAGATTTTGCAACTTACTACTGTCAACAGACTTCTACTTATCCT

GGTACGTTCGGCCAAGGGACCAAGGTGGAAATCAAA

Clone 1 Protein (SEQ ID NO. 2):
EVQLLESGGGLVQPGGSLRLSCAASGFTFSSYAMSWVRQAPGKGLEWVSSISDYGNTT

AYADSVKGRFTISRDNSKNTLYLQMNSLRAEDTAVYYCAKNANYFDYWGQGTLVTVS

SGGGGSGGGGSGGGGSTDIQMTQSPSSLSASVGDRVTITCRASQSISSYLNWYQQKPGK

APKLLIYDASSLQSGVPSRFSGSGSGTDFTLTISSLQPEDFATYYCQQTSTYPGTFGQGTK

VEIK

Clone 3 DNA (SEQ ID NO. 3):
GAGGTGCAGCTGTTGGAGTCTGGGGGAGGCTTGGTACAGCCTGGGGGGTCCCTGAG

ACTCTCCTGTGCAGCCTCTGGATTCACCTTTAGCAGCTATGCCATGAGCTGGGTCCG

CCAGGCTCCAGGGAAGGGGCTGGAGTGGGTCTCATCTATTTCTTCTTATGGTTCTTAT

ACAGGTTACGCAGACTCCGTGAAGGGCCGGTTCACCATCTCCAGAGACAATTCCAA

GAACACGCTGTATCTGCAAATGAACAGCCTGAGAGCCGAGGACACGGCCGTATATT

ACTGTGCGAAAAATGGTTATGCTTTTGACTACTGGGGCCAGGGAACCCTGGTCACCG

TCTCGAGCGGTGGAGGCGGTTCAGGCGGAGGTGGCAGCGGCGGTGGCGGGTCGACG

GACATCCAGATGACCCAGTCTCCATCCTCCCTGTCTGCATCTGTAGGAGACAGAGTC

ACCATCACTTGCCGGGCAAGTCAGAGCATTAGCAGCTATTTAAATTGGTATCAGCAG

AAACCAGGGAAAGCCCCTAAGCTCCTGATCTATGGTGCATCCGCTTTGCAAAGTGGG

GTCCCATCAAGGTTCAGTGGCAGTGGATCTGGGACAGATTTCACTCTCACCATCAGC

AGTCTGCAACCTGAAGATTTTGCAACTTACTACTGTCAACAGAATGATGCTTCTCCT

AATACGTTCGGCCAAGGGACCAAGGTGGAAATCAAA

Clone 3 Protein (SEQ ID NO. 4):
EVQLLESGGGLVQPGGSLRLSCAASGFTFSSYAMSWVRQAPGKGLEWVSSISSYGSYTG

YADSVKGRFTISRDNSKNTLYLQMNSLRAEDTAVYYCAKNGYAFDYWGQGTLVTVSS

GGGGSGGGGSGGGGSTDIQMTQSPSSLSASVGDRVTITCRASQSISSYLNWYQQKPGKA

PKLLIYGASALQSGVPSRFSGSGSGTDFTLTISSLQPEDFATYYCQQNDASPNTFGQGTK

VEIK

Clone 6 DNA (SEQ ID NO. 5):
GAGGTGCAGCTGTTGGAGTCTGGGGGAGGCTTGGTACAGCCTGGGGGGTCCCTGAG

ACTCTCCTGTGCAGCCTCTGGATTCACCTTTAGCAGCTATGCCATGAGCTGGGTCCG

-continued

```
CCAGGCTCCAGGGAAGGGGCTGGAGTGGGTCTCAACTATTTCTACTTATGGTGATTA

TACAACTTACGCAGACTCCGTGAAGGGCCGGTTCACCATCTCCAGAGACAATTCCAA

GAACACGCTGTATCTGCAAATGAACAGCCTGAGAGCCGAGGACACGGCCGTATATT

ACTGTGCGAAAGGTAGTTATACTTTTGACTACTGGGGCCAGGGAACCCTGGTCACCG

TCTCGAGCGGTGGAGGCGGTTCAGGCGGAGGTGGCAGCGGCGGTGGCGGGTCGACG

GACATCCAGATGACCCAGTCTCCATCCTCCCTGTCTGCATCTGTAGGAGACAGAGTC

ACCATCACTTGCCGGGCAAGTCAGAGCATTAGCAGCTATTTAAATTGGTATCAGCAG

AAACCAGGGAAAGCCCCTAAGCTCCTGATCTATTCTGCATCCTATTTGCAAAGTGGG

GTCCCATCAAGGTTCAGTGGCAGTGGATCTGGGACAGATTTCACTCTCACCATCAGC

AGTCTGCAACCTGAAGATTTTGCAACTTACTACTGTCAACAGTCTAATGCTACTCCTT

CTACGTTCGGCCAAGGGACCAAGGTGGAAATCAAA
```

Clone 6 Protein (SEQ ID NO. 6):
```
EVQLLESGGGLVQPGGSLRLSCAASGFTFSSYAMSWVRQAPGKGLEWVSTISTYGDYTT

YADSVKGRFTISRDNSKNTLYLQMNSLRAEDTAVYYCAKGSYTFDYWGQGTLVTVSSG

GGGSGGGGSGGGGSTDIQMTQSPSSLSASVGDRVTITCRASQSISSYLNWYQQKPGKAP

KLLIYSASYLQSGVPSRFSGSGSGTDFTLTISSLQPEDFATYYCQQSNATPSTFGQGTKVEI

KVEIK
```

Clone 10 DNA (SEQ ID NO. 7):
```
GAGGTGCAGCTGTTGGAGTCTGGGGGAGGCTTGGTACAGCCTGGGGGGTCCCTGAG

ACTCTCCTGTGCAGCCTCTGGATTCACCTTTAGCAGCTATGCCATGAGCTGGGTCCG

CCAGGCTCCAGGGAAGGGGCTGGAGTGGGTCTCAGGTATTACTAATTATGGTTATAC

TACATATTACGCAGACTCCGTGAAGGGCCGGTTCACCATCTCCAGAGACAATTCCAA

GAACACGCTGTATCTGCAAATGAACAGCCTGAGAGCCGAGGACACGGCCGTATATT

ACTGTGCGAAATCTTCTTATTCTTTTGACTACTGGGGCCAGGGAACCCTGGTCACCG

TCTCGAGCGGTGGAGGCGGTTCAGGCGGAGGTGGCAGCGGCGGTGGCGGGTCGACG

GACATCCAGATGACCCAGTCTCCATCCTCCCTGTCTGCATCTGTAGGAGACAGAGTC

ACCATCACTTGCCGGGCAAGTCAGAGCATTAGCAGCTATTTAAATTGGTATCAGCAG

AAACCAGGGAAAGCCCCTAAGCTCCTGATCTATGCTGCATCCGCTTTGCAAAGTGGG

GTCCCATCAAGGTTCAGTGGCAGTGGATCTGGGACAGATTTCACTCTCACCATCAGC

AGTCTGCAACCTGAAGATTTTGCAACTTACTACTGTCAACAGTCTGCTTATTATCCTG

ATACGTTCGGCCAAGGGACCAAGGTGGAAATCAAA
```

Clone 10 Protein (SEQ ID NO. 8):
```
EVQLLESGGGLVQPGGSLRLSCAASGFTFSSYAMSWVRQAPGKGLEWVSGITNYGYTT

YYADSVKGRFTISRDNSKNTLYLQMNSLRAEDTAVYYCAKSSYSFDYWGQGTLVTVSS

GGGGSGGGGSGGGGSTDIQMTQSPSSLSASVGDRVTITCRASQSISSYLNWYQQKPGKA

PKLLIYAASALQSGVPSRFSGSGSGTDFTLTISSLQPEDFATYYCQQSAYYPDTFGQGTK

VEIK
```

Clone 13 DNA (SEQ ID NO. 9):
```
GAGGTGCAGCTGTTGGAGTCTGGGGGAGGCTTGGTACAGCCTGGGGGGTCCCTGAG

ACTCTCCTGTGCAGCCTCTGGATTCACCTTTAGCAGCTATGCCATGAGCTGGGTCCG

CCAGGCTCCAGGGAAGGGGCTGGAGTGGGTCTCATCTATTAATTCTGCTGGTGGTTC

TACATATTACGCAGACTCCGTGAAGGGCCGGTTCACCATCTCCAGAGACAATTCCAA

GAACACGCTGTATCTGCAAATGAACAGCCTGAGAGCCGAGGACACGGCGGTATATT
```

-continued

```
ACTGTGCGAAAAATTCTGCTTATTTTGACTACTGGGGCCAGGGAACCCTGGTCACCG

TCTCGAGCGGTGGAGGCGGTTCAGGCGGAGGTGGCAGCGGCGGTGGCGGGTCGACG

GACATCCAGATGACCCAGTCTCCATCCTCCCTGTCTGCATCTGTAGGAGACAGAGTC

ACCATCACTTGCCGGGCAAGTCAGAGCATTAGCAGCTATTTAAATTGGTATCAGCAG

AAACCAGGGAAAGCCCCTAAGCTCCTGATCTATGATGCATCCAATTTGCAAAGTGG

GGTCCCATCAAGGTTCAGTGGCAGTGGATCTGGGACAGATTTCACTCTCACCATCAG

CAGTCTGCAACCTGAAGATTTTGCAACTTACTACTGTCAACAGACTGATACTTATCC

TACTACGTTCGGCCAAGGGACCAAGGTGGAAATCAAA
```

Clone 13 Protein (SEQ ID NO. 10):
```
EVQLLESGGGLVQPGGSLRLSCAASGFTFSSYAMSWVRQAPGKGLEWVSSINSAGGSTY

YADSVKGRFTISRDNSKNTLYLQMNSLRAEDTAVYYCAKNSAYFDYWGQGTLVTVSS

GGGGSGGGGSGGGGSTDIQMTQSPSSLSASVGDRVTITCRASQSISSYLNWYQQKPGKA

PKLLIYDASNLQSGVPSRFSGSGSGTDFTLTISSLQPEDFATYYCQQTDTYPTTFGQGTKV

EIK
```

Clone 17 DNA (SEQ ID NO. 11):
```
GAGGTGCAGCTGTTGGAGTCTGGGGGAGGCTTGGTACAGCCTGGGGGGTCCCTGAG

ACTCTCCTGTGCAGCCTCTGGATTCACCTTTAGCAGCTATGCCATGAGCTGGGTCCG

CCAGGCTCCAGGGAAGGGGCTGGAGTGGGTCTCAAGTATTTCTACTTCTGGTAGTTA

TACAGCTTACGCAGACTCCGTGAAGGGCCGGTTCACCATCTCCAGAGACAATTCCAA

GAACACGCTGTATCTGCAAATGAACAGCCTGAGAGCCGAGGACACGGCCGTATATT

ACTGTGCGAAAGGTGGTTATACTTTTGACTACTGGGGCCAGGGAACCCTGGTCACCG

TCTCGAGCGGTGGAGGCGGTTCAGGCGGAGGTGGCAGCGGCGGTGGCGGGTCGACG

GACATCCAGATGACCCAGTCTCCATCCTCCCTGTCTGCATCTGTAGGAGACAGAGTC

ACCATCACTTGCCGGGCAAGTCAGAGCATTAGCAGCTATTTAAATTGGTATCAGCAG

AAACCAGGGAAAGCCCCTAAGCTCCTGATCTATTCTGCATCCACTTTGCAAAGTGGG

GTCCCATCAAGGTTCAGTGGCAGTGGATCTGGGACAGATTTCACTCTCACCATCAGC

AGTCTGCAACCTGAAGATTTTGCAACTTACTACTGTCAACAGAGTGATGGTAATCCT

ACTACGTTCGGCCAAGGGACCAAGGTGGAAATCAAA
```

Clone 17 Protein (SEQ ID NO. 12):
```
EVQLLESGGGLVQPGGSLRLSCAASGFTFSSYAMSWVRQAPGKGLEWVSSISTSGSYTA

YADSVKGRFTISRDNSKNTLYLQMNSLRAEDTAVYYCAKGGYTFDYWGQGTLVTVSS

GGGGSGGGGSGGGGSTDIQMTQSPSSLSASVGDRVTITCRASQSISSYLNWYQQKPGKA

PKLLIYSASTLQSGVPSRFSGSGSGTDFTLTISSLQPEDFATYYCQQSDGNPTTFGQGTKV

EIK
```

Clone 21 DNA (SEQ ID NO. 13):
```
GAGGTGCAGCTGTTGGAGTCTGGGGGAGGCCTCTGGTACAGCCTGGGGGGTCCCTG

AGACTCTCCTGCGCAGCCTCTGGATTCCACCTTTAGCAGCTATGCCATGACCGGGTC

CCCCAGGCTCCAGGGAAGGGGCTGGAGTGGGTCTCAGGTATTTCGAATCGGGGTAA

GTAGACAATTTACGCAGACTCCGTGAAGGGCCGGTTCACCATCTCCAGAGACAATTC

CAAGAACACGCTGTATCCTGCAAATGAACAGCCTGAGAGCCGAGGACACGGCCGTA

TATTACTGTGCGAAACATAATGCGCATTTTGACTACTGGGGCCAGGGAACCCTGGTC

ACCGTCTCGAGCGGTGGAGGCGGTTCAGGCGGAGGTGGCAGCGGCGGTGGCGGGTC
```

```
-continued
GACGGACATCCAGATGACCCAGTCTCCATCCTCCCTGTCTGCATCTGTAGGAGACAG

AGTCACCATCACTTGCCGGGCAAGTCAGAGCATTAGCAGCTATTTAAATTGGTATCA

GCAGAAACCAGGGAAAGCCCCTAAGCTCCTGATCTATAAGGCATCCAGGTTGCAAA

GTGGGGTCCCATCAAGGTTCAGTGGCAGTGGATCTGGGACAGATTTCACTCTCACCA

TCAGCAGTCTGCAACCTGAAGATTTTGCAACTTACTACTGTCAACAGAGTGCGATGG

TGCCTCCGACGTTCGGCCAAGGGACCAAGGTGGAAATCAAA

Clone 21 Protein (SEQ ID NO. 14):
EVQLLESGGGLVQPGGSLRLSCAASGFTFSSYAMSWVRQAPGKGLEWVSSISYSGAYTA

YADSVNGRFTISRDNSKNTLYLQMNSLRAEDTAVYYCAKSGTDFDYWGQGTLVTVSSG

GGGSGGGGSGGGGSTDIQMTQSPSSLSASVGDRVTITCRASQSISSYLNWYQQKPGKAP

KLLIYGASNLQSGVPSRFSGSGSGTDFTLTISSLQPEDFATYYCQQSNYDPSTFGQGTKVE

IK
```

Expression vectors were constructed for each of the seven scFv proteins. After that, the cell lysates were coated for ELISA. Soluble ELISA was then conducted using the cell lysates from both 30° C. and 37° C. Compared to the control, differences were readily observed in all 7 clones. Among the 7 positive clones, clones 1, 6 and 13 were much stronger than the others.

ELISA with titration was conducted on soluble scFv produced from the seven positive clones to rank their ability to bind MOG. The 7 scFvs were subcloned into pET-26b to be constructed as scFv-myc-6×His format. The purity of the 7 scFvs induced at 16° C. was >85% while the purity when induced at 37° C. was lower. Accordingly, 16° C. was determined to be a more suitable condition for production. QC ELISA was conducted to analyze the binding ability to the target MOG for each of the seven scFvs. Compared to the control, differences were readily found in each of the 7 positive clones (clone 1, 3, 6, 10, 13, 17, 21). Among the 7 positive clones, three clones (clone 3, 6 and 17) indicated stronger binding ability to the target.

Figure 8:
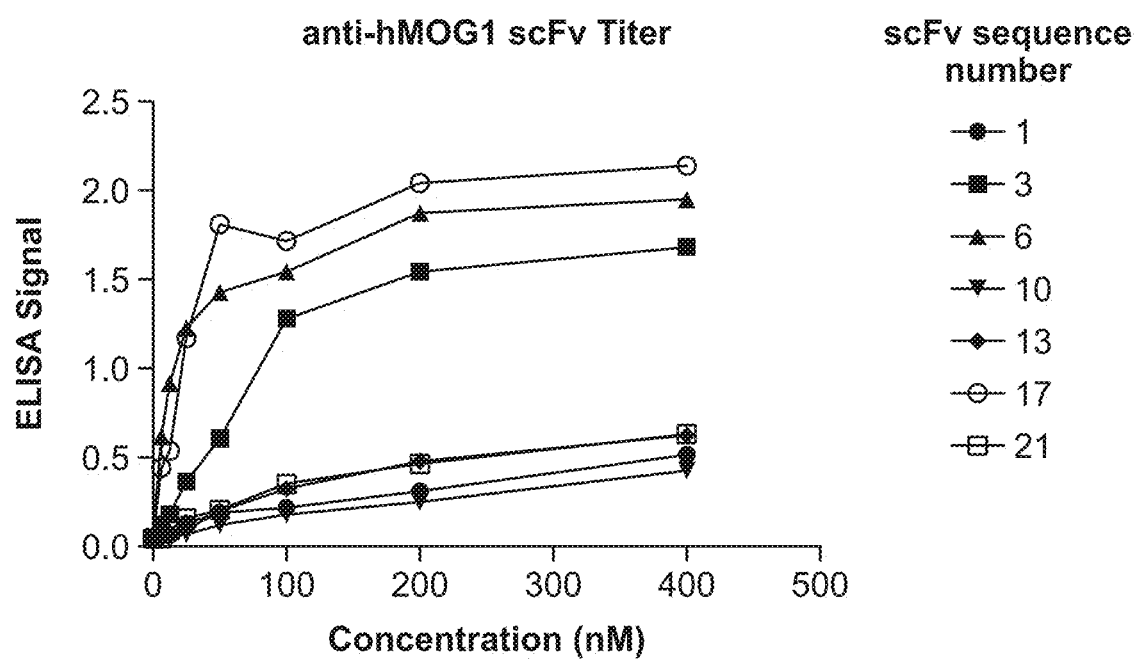

QC ELISA titration for each of the 7 clones induced at 16° C. was conducted. Seven different concentrations of the 7 clones were employed for ELISA titration. The results indicated that all the 7 clones can specifically bind to the target MOG. Among the 7 clones, clone 3, 6 and 17 still indicated stronger binding ability to the target. The results are shown in FIG. 8 illustrating that the anti-hMOG 1 scFv of clone 17 exhibited the strongest binding followed by that of clone 6 and then clone 3. The remaining four clones exhibited significantly weaker binding than that of clones 17, 6, and 3.

What is claimed is:

1. A composition comprising a plurality of engineered regulatory T cells (Tregs),
   wherein the engineered Tregs of the plurality of engineered Tregs are $CD4^+CD127^-CD25^+FOXP3^+$ cells,
   wherein each engineered Treg of the plurality of engineered Tregs expresses a chimeric antigen receptor (CAR) that specifically binds to a glial cell marker,
   wherein the CAR comprises a single-chain variable fragment (scFv) comprising the 6 CDRs present within SEQ ID NO:12, wherein the 6 CDRs are Kabat-defined CDRs.

2. The composition of claim 1, wherein the 6 CDRs are
   (a) SYAMS (CDR-H1) (SEQ ID NO: 15);
   (b) SISTSGSYTAYADSVKG (CDR-H2) (SEQ ID NO: 16);
   (c) GGYTFDY (CDR-H3) (SEQ ID NO: 17);
   (d) RASQSISSYLN (CDR-L1) (SEQ ID NO: 18);
   (e) SASTLQS (CDR-L2) (SEQ ID NO: 19); and
   (f) QQSDGNPTT (CDR-L3) (SEQ ID NO: 20):
   and wherein the composition is a pharmaceutical composition.

3. The composition of claim 2, wherein the scFv has at least 99% sequence identity to SEQ ID NO:12.

4. The composition of claim 3, wherein the scFv is capable of specifically binding to the glial cell marker, myelin oligodendrocyte glycoprotein (MOG).

5. The composition of claim 4, wherein the CAR is capable of directing the engineered Tregs to a glial target cell that expresses MOG.

6. A composition comprising a plurality of engineered regulatory T cells (Tregs),
   wherein the engineered Tregs of the plurality of engineered Tregs are $CD4^+CD127^-CD25^+FOXP3^+$ cells,
   wherein each engineered Treg of the plurality of engineered Tregs expresses a chimeric antigen receptor (CAR) that specifically binds to a glial cell marker,
   wherein the CAR comprises a single-chain variable fragment (scFv) comprising the 6 CDRs present within SEQ ID NO:6, wherein the 6 CDRs are Kabat-defined CDRs.

7. The composition of claim 6, wherein the 6 CDRs are:
   (a) SYAMS (CDR-H1) (SEQ ID NO: 15);
   (b) TISTYGDYTTYADSVKG (CDR-H2) (SEQ ID NO: 21);
   (c) GSYTFDY (CDR-H3) (SEQ ID NO: 22);
   (d) RASQSISSYLN (CDR-L1) (SEQ ID NO: 18);
   (e) SASYLQS (CDR-L2) (SEQ ID NO: 23); and
   (f) QQSNATPST (CDR-L3) (SEQ ID NO: 24):
   and wherein the composition is a pharmaceutical composition.

8. The composition of claim 7, wherein the scFv has at least 99% sequence identity to SEQ ID NO:6.

9. The composition of claim 8, wherein the scFv is capable of specifically binding to the glial cell marker, myelin oligodendrocyte glycoprotein (MOG).

10. The composition of claim 9, wherein the CAR is capable of directing the engineered Tregs to a glial target cell that expresses MOG.

* * * * *

UNITED STATES PATENT AND TRADEMARK OFFICE
CERTIFICATE OF CORRECTION

PATENT NO. : 12,173,030 B2
APPLICATION NO. : 17/041835
DATED : December 24, 2024
INVENTOR(S) : Philip G. Ashton-Rickardt Page 1 of 1

It is certified that error appears in the above-identified patent and that said Letters Patent is hereby corrected as shown below:

In the Claims

In Column 45, in Claim 2, Line 38, delete "are" and insert -- are: --, therefor.

In Column 45, in Claim 2, Line 45, delete "(SEQ ID NO: 20):" and insert -- (SEQ ID NO: 20); --, therefor.

In Column 46, in Claim 7, Line 44, delete "(SEQ ID NO: 24):" and insert -- (SEQ ID NO: 24); --, therefor.

Signed and Sealed this
Twenty-second Day of April, 2025

Coke Morgan Stewart
*Acting Director of the United States Patent and Trademark Office*

SEQUENCE LISTING

<160> NUMBER OF SEQ ID NOS: 24

<210> SEQ ID NO 1
<211> LENGTH: 717
<212> TYPE: DNA
<213> ORGANISM: Artificial Sequence
<220> FEATURE:
<223> OTHER INFORMATION: Synthesized

<400> SEQUENCE: 1

```
gaggtgcagc tgttggagtc tggggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcaagt atttctgatt atggtaatac tacagcttac     180
gcagactccg tgaagggccg gttcaccatc tccagagaca attccaagaa cacgctgtat     240
ctgcaaatga acagcctgag agccgaggac acggccgtat attactgtgc gaaaaatgct     300
aattattttg actactgggg ccagggaacc ctggtcaccg tctcgagcgg tggaggcggt     360
tcaggcggag gtggcagcgg cggtggcggg tcgacggaca tccagatgac ccagtctcca     420
tcctccctgt ctgcatctgt aggagacaga gtcaccatca cttgccgggc aagtcagagc     480
attagcagct atttaaattg gtatcagcag aaaccaggga agcccctaa gctcctgatc      540 tatgatgcat ccagtttgca aagtggggtc ccatcaaggt tcagtggcag tggatctggg     600
acagatttca ctctcaccat cagcagtctg caacctgaag attttgcaac ttactactgt     660
```

```
caacagactt ctacttatcc tggtacgttc ggccaaggga ccaaggtgga aatcaaa    717
```

<210> SEQ ID NO 2
<211> LENGTH: 239
<212> TYPE: PRT
<213> ORGANISM: Artificial Sequence
<220> FEATURE:
<223> OTHER INFORMATION: Synthesized

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Asp Tyr Gly Asn Thr Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ala Asn Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Asp Ala Ser Ser Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Thr Ser
    210                 215                 220

Thr Tyr Pro Gly Thr Phe Gly Gln Gly Thr Lys Val Glu Ile Lys
225                 230                 235
```

<210> SEQ ID NO 3
<211> LENGTH: 717
<212> TYPE: DNA
<213> ORGANISM: Artificial Sequence
<220> FEATURE:
<223> OTHER INFORMATION: Synthesized

<400> SEQUENCE: 3

```
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg ggctggagtg gtctcatct atttcttctt atggttctta tacaggttac     180
gcagactccg tgaagggccg gttcaccatc tccagagaca attccaagaa cacgctgtat    240
ctgcaaatga acagcctgag agccgaggac acggccgtat attactgtgc gaaaaatggt    300
tatgcttttg actactgggg ccagggaacc ctggtcaccg tctcgagcgg tggaggcggt    360
```
tcaggcggag gtggcagcgg cggtggcggg tcgacggaca tccagatgac ccagtctcca    420
tcctccctgt ctgcatctgt aggagacaga gtcaccatca cttgccgggc aagtcagagc    480
attagcagct atttaaattg gtatcagcag aaaccaggga aagcccctaa gctcctgatc    540
tatggtgcat ccgctttgca aagtggggtc ccatcaaggt tcagtggcag tggatctggg    600
acagatttca ctctcaccat cagcagtctg caacctgaag attttgcaac ttactactgt    660
caacagaatg atgcttctcc taatacgttc ggccaaggga ccaaggtgga aatcaaa      717

<210> SEQ ID NO 4
<211> LENGTH: 239
<212> TYPE: PRT
<213> ORGANISM: Artificial Sequence
<220> FEATURE:
<223> OTHER INFORMATION: Synthesized

<400> SEQUENCE: 4

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Ser Tyr Gly Ser Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Gly Tyr Ala Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser Ala Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Asn Asp
    210                 215                 220

Ala Ser Pro Asn Thr Phe Gly Gln Gly Thr Lys Val Glu Ile Lys
225                 230                 235

<210> SEQ ID NO 5
<211> LENGTH: 717
<212> TYPE: DNA
<213> ORGANISM: Artificial Sequence
<220> FEATURE:
<223> OTHER INFORMATION: Synthesized

<400> SEQUENCE: 5
gaggtgcagc tgttggagtc tgggggaggc ttggtacagc ctggggggtc cctgagactc     60

```
tcctgtgcag cctctggatt cacctttagc agctatgcca tgagctgggt ccgccaggct    120
ccagggaagg ggctggagtg ggtctcaact atttctactt atggtgatta taacttac     180 gcagactccg tgaagggccg gttcaccatc tccagagaca attccaagaa cacgctgtat    240
ctgcaaatga acagcctgag agccgaggac acggccgtat attactgtgc gaaaggtagt   300
tatacttttg actactgggg ccagggaacc ctggtcaccg tctcgagcgg tggaggcggt   360
tcaggcggag gtggcagcgg cggtggcggg tcgacggaca tccagatgac ccagtctcca   420 tcctcccctgt ctgcatctgt aggagacaga gtcaccatca cttgccgggc aagtcagagc  480
attagcagct atttaaattg gtatcagcag aaaccaggga agcccctaa gctcctgatc    540 tattctgcat cctatttgca aagtggggtc ccatcaaggt tcagtggcag tggatctggg   600
acagatttca ctctcaccat cagcagtctg caacctgaag attttgcaac ttactactgt   660
caacagtcta atgctactcc ttctacgttc ggccaaggga ccaaggtgga aatcaaa      717
```

<210> SEQ ID NO 6
<211> LENGTH: 243
<212> TYPE: PRT
<213> ORGANISM: Artificial Sequence
<220> FEATURE:
<223> OTHER INFORMATION: Synthesized

<400> SEQUENCE: 6

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Thr Ile Ser Thr Tyr Gly Asp Tyr Thr Thr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Ser Tyr Thr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ser Ala Ser Tyr Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Asn
    210                 215                 220

Ala Thr Pro Ser Thr Phe Gly Gln Gly Thr Lys Val Glu Ile Lys Val
225                 230                 235                 240

Glu Ile Lys
```

<210> SEQ ID NO 7
<211> LENGTH: 717
<212> TYPE: DNA
<213> ORGANISM: Artificial Sequence
<220> FEATURE:
<223> OTHER INFORMATION: Synthesized

<400> SEQUENCE: 7

```
gaggtgcagc tgttggagtc tgggggaggc ttggtacagc ctgggggggtc cctgagactc      60
tcctgtgcag cctctggatt cacctttagc agctatgcca tgagctgggt ccgccaggct     120
ccagggaagg ggctggagtg ggtctcaggt attactaatt atggttatac tacatattac     180
gcagactccg tgaagggccg gttcaccatc tccagagaca attccaagaa cacgctgtat     240
ctgcaaatga acagcctgag agccgaggac acggccgtat attactgtgc gaaatcttct     300
tattcttttg actactgggg ccagggaacc ctggtcaccg tctcgagcgg tggaggcggt     360
tcaggcggag gtggcagcgg cggtggcggg tcgacggaca tccagatgac ccagtctcca     420
tcctccctgt ctgcatctgt aggagacaga gtcaccatca cttgccgggc aagtcagagc     480
attagcagct atttaaattg gtatcagcag aaaccaggga agcccctaa gctcctgatc     540
tatgctgcat ccgctttgca aagtggggtc ccatcaaggt tcagtggcag tggatctggg     600
acagatttca ctctcaccat cagcagtctg caacctgaag attttgcaac ttactactgt     660
caacagtctg cttattatcc tgatacgttc ggccaaggga ccaaggtgga aatcaaa      717
```

<210> SEQ ID NO 8
<211> LENGTH: 239
<212> TYPE: PRT
<213> ORGANISM: Artificial Sequence
<220> FEATURE:
<223> OTHER INFORMATION: Synthesized

<400> SEQUENCE: 8

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Thr Asn Tyr Gly Tyr Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Ser Tyr Ser Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ala Ala Ser Ala Leu Gln Ser Gly Val Pro Ser

```
            180                 185                 190
Arg Phe Ser Gly Ser Gly Ser Gly Thr Asp Phe Thr Leu Thr Ile Ser
                195                 200                 205

Ser Leu Gln Pro Glu Asp Phe Ala Thr Tyr Tyr Cys Gln Gln Ser Ala
    210                 215                 220

Tyr Tyr Pro Asp Thr Phe Gly Gln Gly Thr Lys Val Glu Ile Lys
225                 230                 235
```

<210> SEQ ID NO 9
<211> LENGTH: 717
<212> TYPE: DNA
<213> ORGANISM: Artificial Sequence
<220> FEATURE:
<223> OTHER INFORMATION: Synthesized

<400> SEQUENCE: 9

```
gaggtgcagc tgttggagtc tgggggaggc ttggtacagc ctggggggtc cctgagactc     60
tcctgtgcag cctctggatt cacctttagc agctatgcca tgagctgggt ccgccaggct    120
ccagggaagg gctggagtg gtctcatct attaattctg ctggtggttc tacatattac     180
gcagactccg tgaagggccg gttcaccatc tccagagaca attccaagaa cacgctgtat    240
ctgcaaatga acagcctgag agccgaggac acggcggtat attactgtgc gaaaaattct    300
gcttattttg actactgggg ccagggaacc ctggtcaccg tctcgagcgg tggaggcggt    360
tcaggcggag gtggcagcgg cggtggcggg tcgacggaca tccagatgac ccagtctcca    420
tcctcccctgt ctgcatctgt aggagacaga gtcaccatca cttgccgggc aagtcagagc    480
attagcagct atttaaattg gtatcagcag aaaccaggga agcccctaa gctcctgatc    540
tatgatgcat ccaatttgca aagtgggtc ccatcaaggt tcagtggcag tggatctggg    600
acagatttca ctctcaccat cagcagtctg caacctgaag attttgcaac ttactactgt    660
caacagactg atacttatcc tactacgttc ggccaaggga ccaaggtgga aatcaaa      717
```

<210> SEQ ID NO 10
<211> LENGTH: 239
<212> TYPE: PRT
<213> ORGANISM: Artificial Sequence
<220> FEATURE:
<223> OTHER INFORMATION: Synthesized

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asn Ser Ala Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asn Ser Ala Tyr Phe Asp Tyr Trp Gly Gln Gly Thr Leu Val
            100                 105                 110

Thr Val Ser Ser Gly Gly Gly Gly Ser Gly Gly Gly Gly Ser Gly Gly
        115                 120                 125
```

Gly Gly Ser Thr Asp Ile Gln Met Thr Gln Ser Pro Ser Ser Leu Ser
            130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Asp Ala Ser Asn Leu Gln Ser Gly Val Pro Ser
                180                 185                 190

Arg Phe Ser Gly Ser Gly Ser Gly Thr Asp Phe Thr Leu Thr Ile Ser
            195                 200                 205

Ser Leu Gln Pro Glu Asp Phe Ala Thr Tyr Tyr Cys Gln Gln Thr Asp
            210                 215                 220

Thr Tyr Pro Thr Thr Phe Gly Gln Gly Thr Lys Val Glu Ile Lys
225                 230                 235

<210> SEQ ID NO 11
<211> LENGTH: 717
<212> TYPE: DNA
<213> ORGANISM: Artificial Sequence
<220> FEATURE:
<223> OTHER INFORMATION: Synthesized

<400> SEQUENCE: 11
gaggtgcagc tgttggagtc tgggggaggc ttggtacagc ctgggggtc cctgagactc      60 tcctgtgcag cctctggatt cacctttagc agctatgcca tgagctgggt ccgccaggct    120
ccagggaagg gctggagtg gtctcaagt atttctactt ctggtagtta tacagcttac      180
gcagactccg tgaagggccg gttcaccatc tccagagaca attccaagaa cacgctgtat    240
ctgcaaatga acagcctgag agccgaggac acggccgtat attactgtgc gaaaggtggt    300
tatacttttg actactgggg ccagggaacc ctggtcaccg tctcgagcgg tggaggcggt    360
tcaggcggag gtggcagcgg cggtggcggg tcgacggaca tccagatgac ccagtctcca    420
tcctccctgt ctgcatctgt aggagacaga gtcaccatca cttgccgggc aagtcagagc    480
attagcagct atttaaattg gtatcagcag aaaccaggga agcccctaa gctcctgatc     540 tattctgcat ccactttgca aagtggggtc ccatcaaggt tcagtggcag tggatctggg    600
acagatttca ctctcaccat cagcagtctg caacctgaag attttgcaac ttactactgt    660
caacagagtg atggtaatcc tactacgttc ggccaaggga ccaaggtgga aatcaaa       717

<210> SEQ ID NO 12
<211> LENGTH: 239
<212> TYPE: PRT
<213> ORGANISM: Artificial Sequence
<220> FEATURE:
<223> OTHER INFORMATION: Synthesized

<400> SEQUENCE: 12

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Ser Thr Ser Gly Ser Tyr Thr Ala Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Gly Tyr Thr Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Thr Asp Ile Gln Met Thr Gln Ser Pro Ser Ser Leu Ser
130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Ser Ala Ser Thr Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Asp
    210                 215                 220

Gly Asn Pro Thr Thr Phe Gly Gln Gly Thr Lys Val Glu Ile Lys
225                 230                 235

<210> SEQ ID NO 13
<211> LENGTH: 720
<212> TYPE: DNA
<213> ORGANISM: Artificial Sequence
<220> FEATURE:
<223> OTHER INFORMATION: Synthesized

<400> SEQUENCE: 13
gaggtgcagc tgttggagtc tgggggaggc ctctggtaca gcctgggggg tccctgagac      60
tctcctgcgc agcctctgga ttccaccttt agcagctatg ccatgaccgg gtccccagg     120
ctccagggaa ggggctggag tgggtctcag gtatttcgaa tcggggtaag tagacaattt     180
acgcagactc cgtgaaggc cggttcacca tctccagaga caattccaag aacacgctgt     240
atcctgcaaa tgaacagcct gagagccgag gacacggccg tatattactg tgcgaaacat     300
aatgcgcatt ttgactactg gggccaggga accctggtca ccgtctcgag cggtggaggc     360
ggttcaggcg gaggtggcag cggcggtggc gggtcgacgg acatccagat gacccagtct     420
ccatcctccc tgtctgcatc tgtaggagac agagtcacca tcacttgccg ggcaagtcag     480
agcattagca gctatttaaa ttggtatcag cagaaaccag ggaaagcccc taagctcctg     540
atctataagg catccaggtt gcaaagtggg gtcccatcaa ggttcagtgg cagtggatct     600
gggacagatt tcactctcac catcagcagt ctgcaacctg aagattttgc aacttactac     660
tgtcaacaga gtgcgatggt gcctccgacg ttcggccaag gaccaaggt ggaaatcaaa     720

<210> SEQ ID NO 14
<211> LENGTH: 239
<212> TYPE: PRT
<213> ORGANISM: Artificial Sequence
<220> FEATURE:
<223> OTHER INFORMATION: Synthesized

<400> SEQUENCE: 14

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr

```
                20                  25                  30
Ala Met Ser Trp Val Arg Gln Ala Pro Gly Lys Gly Leu Glu Trp Val
            35                  40                  45

Ser Ser Ile Ser Tyr Ser Gly Ala Tyr Thr Tyr Ala Asp Ser Val
    50                  55                  60

Asn Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ser Gly Thr Asp Phe Asp Tyr Trp Gly Gln Gly Thr Leu Val
            100                 105                 110

Thr Val Ser Ser Gly Gly Gly Ser Gly Gly Gly Ser Gly Gly
        115                 120                 125

Gly Gly Ser Thr Asp Ile Gln Met Thr Gln Ser Pro Ser Ser Leu Ser
    130                 135                 140

Ala Ser Val Gly Asp Arg Val Thr Ile Thr Cys Arg Ala Ser Gln Ser
145                 150                 155                 160

Ile Ser Ser Tyr Leu Asn Trp Tyr Gln Gln Lys Pro Gly Lys Ala Pro
                165                 170                 175

Lys Leu Leu Ile Tyr Gly Ala Ser Asn Leu Gln Ser Gly Val Pro Ser
            180                 185                 190

Arg Phe Ser Gly Ser Gly Ser Gly Thr Asp Phe Thr Leu Thr Ile Ser
        195                 200                 205

Ser Leu Gln Pro Glu Asp Phe Ala Thr Tyr Tyr Cys Gln Gln Ser Asn
    210                 215                 220

Tyr Asp Pro Ser Thr Phe Gly Gln Gly Thr Lys Val Glu Ile Lys
225                 230                 235

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ser Tyr Ala Met Ser
1               5

<210> SEQ ID NO 16
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Ile Ser Thr Ser Gly Ser Tyr Thr Ala Tyr Ala Asp Ser Val Lys
1               5                   10                  15

Gly

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 17

Gly Gly Tyr Thr Phe Asp Tyr
1               5

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Arg Ala Ser Gln Ser Ile Ser Ser Tyr Leu Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Ser Ala Ser Thr Leu Gln Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gln Gln Ser Asp Gly Asn Pro Thr Thr
1               5

<210> SEQ ID NO 21
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Thr Ile Ser Thr Tyr Gly Asp Tyr Thr Thr Tyr Ala Asp Ser Val Lys
1               5                   10                  15

Gly

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ser Tyr Thr Phe Asp Tyr
1               5
```

```
<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ser Ala Ser Tyr Leu Gln Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gln Gln Ser Asn Ala Thr Pro Ser Thr
1               5
```